United States Patent
Rezania

(10) Patent No.: US 10,208,288 B2
(45) Date of Patent: Feb. 19, 2019

(54) DIFFERENTIATION OF HUMAN EMBRYONIC STEM CELLS INTO PANCREATIC ENDOCRINE CELLS

(71) Applicant: Janssen Biotech, Inc., Horsham, PA (US)

(72) Inventor: Alireza Rezania, Horsham, PA (US)

(73) Assignee: Janssen Biotech, Inc., Horsham, PA (US)

( * ) Notice: Subject to any disclaimer, the term of this patent is extended or adjusted under 35 U.S.C. 154(b) by 84 days.

(21) Appl. No.: 15/340,418

(22) Filed: Nov. 1, 2016

(65) Prior Publication Data

US 2017/0044499 A1 Feb. 16, 2017

Related U.S. Application Data

(62) Division of application No. 13/911,829, filed on Jun. 6, 2013, now Pat. No. 10,066,210.

(60) Provisional application No. 61/657,160, filed on Jun. 8, 2012.

(51) Int. Cl.
C12N 5/071 (2010.01)

(52) U.S. Cl.
CPC ........ *C12N 5/0676* (2013.01); *C12N 2501/50* (2013.01); *C12N 2501/998* (2013.01); *C12N 2506/02* (2013.01)

(58) Field of Classification Search
None
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |

(Continued)

FOREIGN PATENT DOCUMENTS

| | | |
|---|---|---|
| CN | 1389565 A | 7/2002 |
| CN | 101611016 A | 7/2002 |

(Continued)

OTHER PUBLICATIONS

Rezania, A. et al. Maturation of human embryonic stem cell-derived pancreatic progenitors into functional islets capable of treating pre-existing diabetes in mice. Diabetes 61, 2016-2029 (2012). (Year: 2012).*

(Continued)

*Primary Examiner* — Blaine Lankford
(74) *Attorney, Agent, or Firm* — Mark R. Warfield

(57) ABSTRACT

The present invention provides methods to promote differentiation of pancreatic endoderm cells to pancreatic endocrine rich clusters and to enhance insulin expression in hormone-expressing cells.

14 Claims, 10 Drawing Sheets

(56) References Cited

U.S. PATENT DOCUMENTS

| | | |
|---|---|---|
| 7,510,873 B2 | 3/2009 | Mistry |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 9,528,090 B2 | 12/2016 | Rezania |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumeisky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0147298 A1 | 6/2005 | Vasudevan et al. |
| 2005/0148070 A1 | 7/2005 | Thomson et al. |
| 2005/0158852 A1 | 7/2005 | Wang et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour et al. |
| 2006/0003313 A1 | 1/2006 | D'Amour et al. |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0122104 A1 | 6/2006 | Presnell et al. |
| 2006/0194321 A1 | 6/2006 | Colman et al. |
| 2006/0148081 A1 | 7/2006 | Kelly et al. |
| 2006/0194315 A1 | 8/2006 | Condie et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |
| 2014/0186953 A1 | 7/2014 | Rezania |

FOREIGN PATENT DOCUMENTS

| | | |
|---|---|---|
| CN | 1602351 A | 3/2005 |
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2005537803 A1 | 12/2005 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 1767433 A1 | 10/1992 |
| RU | 2359030 C1 | 6/2009 |
| RU | 2359671 C2 | 6/2009 |
| WO | WO199219759 A2 | 2/1992 |
| WO | 1996040172 A1 | 12/1996 |
| WO | 199830679 A1 | 7/1998 |
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO200305049 A1 | 6/2003 |
| WO | 2003054169 A1 | 7/2003 |
| WO | 2003062405 A2 | 7/2003 |

(56) References Cited

FOREIGN PATENT DOCUMENTS

| | | |
|---|---|---|
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | 2006088867 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A2 | 9/2007 |
| WO | 2007127927 A2 | 11/2007 |
| WO | 2007136673 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2006102118 A1 | 8/2008 |
| WO | 2008094597 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Rezania, A. et al. Enrichment of human embryonic stem cell-derived NKX6.1-expressing pancreatic progenitor cells accelerates the maturation of insulin-secreting cells in vivo. Stem Cells 31, 2432-2442 (2013). (Year: 2013).*

Abe, et al., Evidence That PI3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

Ackermann, et al., Molecular Regulation of Pancreatic B-Cell Mass Development, Maintenance, and Expansion, Journal of Molecular Endocrinology, 2007, pp. 193-206, vol. 38.

Adams, et al., Proteasome Inhibition in Cancer: Development of PS-341, Seminars in Oncology, 2001, pp. 613-619, vol. 28, No. 6.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Ali, et al., Exploitation of Protein Kinase C: A Useful Target for Cancer Therapy, Cancer Treatment Reviews, 2009, pp. 1-8, vol. 35.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit et al., Human Feeder Layers for Human Embryonic Stem Cells, Biology of Reproduction, Jan. 22, 2003, 2150-2156, 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Dynamic Suspension Culture for Scalable Expansion of Undifferentiated Human Pluripotent Stem Cells, Nature Protocols, Apr. 7, 2011, pp. 572-579, vol. 6, No. 5.

(56) References Cited

OTHER PUBLICATIONS

Amit, et al., Feeder Layer-and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Assady, et al., Insulin Production by Human Embryonic Stem Cells, Diabetes, 2001, pp. 1691-1697, vol. 50.

Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.

Baetge, Production of B-Cells from Human Embryonic Stem Cells, Diabetes, Obesity, Metabolism, 2008, pp. 186-194, vol. 10, Supplement 4.

Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.

Balsam, et al., Haematopoeitic Stem Cells Adopt Mature Haeatopoietic Fates in Ischaemic Myocardium, Nature, Apr. 8, 2004, pp. 668-673, vol. 428, Nature Publishing Group.

Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

Barclay, et al., The Leucocyte Antigen Facts Book, The Leucocyte Antigen Facts Book, 1997, Textbook, 21[sup] edition, Academic Press.

Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.

Beltrami, et al., Adult Cardiac Stem Cells are Multipotent and Support Myocardial Regeneration, Cell, Sep. 19, 2003, pp. 763-776, vol. 114, Cell Press.

Best, et al., Embryonic Stem Cells to Beta-Cells by Understanding Pancreas Development, Molecular and Cellular Endorinology, 2008, pp. 86-94, vol. 288.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139; vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, pp. 998-1003, vol. 100-3, National Academy of Sciences.

Bo, et al., Research Progress of Pancreatic Islet Development and Pancreatic Stem Cells, Journal of Clinical Surgery, 2009, pp. 208-210, vol. 17, No. 3.

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, pp. 7999-8004, vol. 97-14, National Academy of Sciences.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, pp. 86-93, vol. 269-1, US.

Brambrink., et al, Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, pp. 381-382, vol. 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, 3016-3020, 10.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870. D0I10/1095.

Chetty, et al., a Simple Tool ti improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

(56) References Cited

OTHER PUBLICATIONS

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al, Production of pancreatic hormone, Production of pancreatic hormone, 2006, pp. 1392-1401, vol. 24.

Damy, et al., Increased Neuronal Nitric Oxide Synthase-Derived NO Production in the Failing Human Heart, Research Letters, Apr. 24, 2004, pp. 1365-1367, vol. 363.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

De Rosa, 11-color, 13-parameter flow cytometry: Identification of . . . , Nature, Feb. 1, 2001, 245-248, 7-2, Nature Publishing Group, US.

Dekker, et al., Adhesion of Endothelial Cells and Adsorption of Serum Proteins on Gas Plasma-Treated Polytetrafluoroethylene, Biomaterials, 1991, pp. 130-138, vol. 12.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Recurrent Gain of Chromosomes 17q and 12 in Cultured Human Embryonic Stern Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dufour, et al., Development of an Ectopic Site for Islet Transplantation Using Biodegradable Scaffolds, Tissue Engineering, 2005, pp. 1323-1331, vol. 11, No. 9/10.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Eguizabal, et al., Embryonic Stem Cells/Induced Pluriptent Stem Complete Meiosis from Human Induced Pluripotent Stem Cells, Stem Cells, 2011, pp. 1186-1195, vol. 29.

Ellerstrom, et al., Derivation of a Xeno-Free Human Embryonic Stem Cell Line, Stem Cells, 2006, pp. 2170-2176, vol. 24.

Ellerstrom, et al., Facilitated Expansion of Human Embryonic Stem Cells by Single-Cell Enzymatic Dissociation, Stem Cells, 2007, pp. 1690-1696, vol. 25, No. 7.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12 Association for Research in Vision and Ophthamology.

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low 02 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, pp. 727-732, vol. 137-2, American Society of Immunologists, US.

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

Florio, et al., Activin A Stimulates Insulin Secretion in Cultured Human Pancreatic Islets, J. Eridocrinol. Invest., 2000, pp. 231-234, vol. 23.

Fok, et al., Shear-Controlled Single-Step Mouse Embryonic Stem Cell Expansion and Embryoid Body-Based Differentiation, Stem Cells, 2005, pp. 1333-1342, vol. 23.

Foster, et al., Differentiation of Transplanted Microencapsulated Fetal Pancreatic Cells, Experimental Transplantation, Jun. 15, 2007, pp. 1440-1448, vol. 83, No. 11.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.

Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.

Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, pp. 16806-16811, vol. 103-45, National Academy of Sciences, US.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.

Gershengorn et al., Epithelial-to-Mesenchyrnal Transition Generates Proliferative Human Islet Precursor Cells, Science, Dec. 24, 2004, pp. 2261-2264, vol. 306, US.

Gibco, Solutions for Life Science Research and Drug Discovery, Catalogue Cell Culture Products, 2004-2005, pp. 1-4E. 281406 26 5 27.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.

(56) References Cited

OTHER PUBLICATIONS

Gittest, Developmental Biology of the Pancreas: A comprehensive Review, Developmental Biology, 2009, pp. 4-35, vol. 326, No. 1.
Gordon Weir, Do stem cells hold the key to creation of a cure for diabetes?, Diabetes Voice, 2008, pp. 29-31, Edition 53, No. 2.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Gregg Duester, Retionoic Acid Synthesis and Signaling During Early Organogenesis, Cell, 2008, pp. 921-931, vol. 134.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, pp. 1511-1522, vol. 101, Rockefeller University Press.
Hainsworth, et al., Retinal Capillar Basement Membrane Thickening in a Porcine Model of Diabetes Mellitus, Comp Med, 2002, pp. 523-529, vol. 52.
Hamann, et al., Phenotypic and Functional Separation of Memory and and Effector Human CD8+ T Cells, Journal of Experimental Medicine, Mar. 11, 1997, pp. 1407-1418, vol. 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, vol. 3, Issue 8.
Harmon, et al., GDF11 Modulates NGN3+ Islet Progenitor Cell Number and Promotes B-Cell Differentiation in Pancreas Development, Development, 2004, pp. 6163-6174, vol. 131.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Hay, et al., Highly Efficient Differentiation of hESCs to Functional Hepatic Endoderm Requires ActivinA and Wnt3a Signaling, PNAS, 2008, pp. 12301-12306, vol. 105, No. 34.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, pp. 33-37, vol. 47, Portland Press Ltd., GB.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322, vol. 127, No. 11.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, pp. 16105-16110, vol. 99-25, National Academy of Sciences.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010,96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No, 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, pp. 544-549, vol. 23, AlphaMed Press.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jafary, et al., Differential effect of activin on mouse embryonic stem cell differentiation in insulin-secreting cells under nestin-positive selection and spontaneous differentiation protocols, Cell Biology International, 2008, pp. 278-286, vol. 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Jiang, et al., In Vitro Derivation of Functional Insulin-Producing Cells from Human Embryonic Stem Cells, Cell Research, 2007, pp. 333-344, vol. 17.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Karvonen, et al., Incidene of Childhood Type 1 Diabetes Worldwide, Diabetes Care, 2000, pp. 1516-1526, vol. 23, No. 10.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.

(56) References Cited

OTHER PUBLICATIONS

Kingsley, The TGF-B Superfamily: New Members, New Receptors, and New Genetic Tests of Function in Different Organisms, Genes & Development, 1994, pp. 133-146, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, pp. 312-318, vol. 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Koyangi et al., Inhibitio nof the Rho/ROCK Pathway Reduces Apoptosis During Transplantatation of Embryonic Stem Cell-Derived Neural Precursors, Journal of Neuroscience Research, Sep. 7, 2007, 270-280, 86, Wiley-Liss, Inc.
Kozikowsk, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, pp. 1124-1126, vol. 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine Immune Cell Surface Markers and Intracellular Phosphoproteins by Flow Cytometry, Journal of Immunology, May 30, 2005, pp. 2357-2365, vol. 175, American Association of Immunologists, Inc., US.
Ku et al., Committing Embryonic Stem Cells to Early Endocrine Pancreas In Vitro, Stem Cells, 2004, pp. 1205-1217, vol. 22, AlphaMed Press.
Kubo et al., Development of definitive endoderm from embryonic stem cells in culture, Development, 2004, pp. 1651-1662, vol. 131, The Company of Biologists.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.
Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Larsen, et al., Use of the Gootingen Minipig as a Model of Diabetes, with Special Focus on Type 1 Diabetes Research, ILAR Journal, 2004, pp. 303-313, vol. 45, No. 3.
Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., PKC—Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Lee, et al., Protein Kinase A- and C-Induced Insulin Release from Ca2+-Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Leon-Quinto, et al., In Vitro Directed Differentiation of Mouse Embryonic Stem Cells into Insulin-Producing Cells, Diabetologia, 2004, pp. 1442-1451, vol. 47, No. 8.
Levenstein et al., Basic Fibroblast Growth Factor Support of Human Embryonic Stem Cell Self-Renewal, Stem Cells, Nov. 10, 2005, 568-574, 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Li, et al., Piuripotency Can be Rapidly and Efficiently Induced in Human Amniotic Fluid-Derived Cells, Human Molecular Genetics, 2009, pp. 4340-4349, vol. 18, No. 22.
Lilja et al., Cyclin-dependent Kinase 5 Promotes Insulin Exocytosis, Journal of Biological Chemistry, Jul. 6, 2001, 34199-34205, 36-7, JBC Papers in Press.
Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Ludwig, et al., Defined Culture Media for Human Embryonic Stem Cells, Embryonic Stem Cells, 2007, pp. 1-16, Springer.
Ludwig, et al., Derivation of Human Embryonic Stem Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, pp. 1389-1394, vol. 292, HighWire Press.
Lund, et al., Cell Transplantation as a Treatment for Retinal Disease, Progress in Retinal and Eye Research, 2001, pp. 415-449, vol. 20, No. 4, Elsevier Science Ltd.
Lund, et al., Retinal Transplantation: Progress and Problems in Clinical Application, Journal of Leukocyte Biology, Aug. 2003, pp. 151-160, vol. 74.
Lyttle, et al., Transcription Factor Expression in the Developing Human Fetal Endocrine Pancreas, Diabetologica, 2006, pp. 1169-1180, vol. 51, Spring-Verlag.

(56) References Cited

OTHER PUBLICATIONS

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.
Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.
Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.
Marshall, et al., Early Micro-and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.
McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, pp. 301-305, vol. 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, pp. 433-440, vol. 22, AlphaMed Press.
Miyazaki et al., Regulated Expression of pdx-1 Promotes In Vitro Differentiation of Insulin-Producing Cells From Embryonic Stem Cells, Diabetes, Apr. 2004, pp. 1030-1037, vol. 53, American Diabetes Association.

Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Veithoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.
Munoz et al, Conventional pluripotency markers, Conventional pluripotency markers, Feb. 7, 2014, pp. 1159-1164, vol. 69.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al., A Method for Single-Cell Sorting and Expansion of Genetically modified Human Embryonic Stem Cells, Stem Cells and Development, 2007, pp. 109-117, vol. 16, Mary Ann Liebert, Inc.
Nie, et al., Scalable Passaging of Adherent Human Pluripotent Stem Cells, PLOS One, 2014, pp. 1-9, vol. 9, Issue 1.
Nishimura, et al., Expression of MafA in Pancreatic Progenitors is Detrimental for Pancreatic Development, Developmental Biology, 2009, pp. 108-120, vol. 333.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One; Jul. 30, 2008, e2841, pp. 1-7, vol. 3, No. 7.
Ouziel-Yahalom, et al., Expansion and Redifferentiation of Adult Human Pancreatic Islet Cells, Biochemical and Biophysical Research Communications, 2006, pp. 291-298, vol. 341.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.

(56) References Cited

OTHER PUBLICATIONS

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Pardo, et al., Corning CellBIND Surface: An Improved Surface for Enhanced Cell Attachment, Corning Technical Report, 2005, 8 page report.

Paris, et al, Embryonic Stem Cells in Domestic Animals, Embryonic Stem Cells in Domestic Animals, Feb. 7, 2014, pp. 516-524, vol. 74.

Park, et al., Effects of Activin A on Pancreatic Ductal Cells in Streptozotocin-Inducted Diabetic Rats, Experimental Transplantation, 2007, pp. 925-930, vol. 83.

Peerani, et al., Niche-Mediated Control of Human Embryonic Stem Cell Self-Renewal and Differentiation, The EMBO Journal, 2007, pp. 4744-4755, vol. 26.

Perrier, et al., Derivation of Midbrain Dopamine Neurons from Human Embryonic Stem Cells, PNAS, Aug. 24, 2004, pp. 12543-12548, vol. 101, No. 34.

Phillips, et al., Attachment and Growth of Human Embryonic Stem Cells on Microcarriers, Journal of Biotechnology, 2008, pp. 24-32, vol. 138.

Phillips, et al., Directed Differentiation of Human Embryonic Stem Cells into the Pancreatic Endocrine Lineage, Stem Cells and Development, 2007, pp. 561-578, vol. 16, No. 4.

Pouton, et al., Embryonic Stem Cells as a Source of Models for Drug Discovery, Nature Reviews Drug Discovery, Aug. 2007, pp. 1474-1776, vol. 6, No. 8.

Prichard, et al., Adult Adipose Derived Stem Cell Attachment to Biomaterials, Biomaterials, 2006, pp. 936-946, vol. 26, No. 6.

Prowse, et al., A Proteome Analysis of Conditioned Media from Human Neonatal Fibroblasts Used in the Maintenance of Human Embryonic Stem Cells, Proteomics, 2005, pp. 978-989, vol. 5.

Prusa, et al., Oct-4-Expressing Cells in Human Amniotic Fluid: a New Source for Stem Cell Research?, Human Reproduction, 2003, pp. 1489-1493, vol. 18, No. 7.

Ptasznik, et al., Phosphatidylinositol 3-Kinase Is a Negative Regulator of Cellular Differentiation, The Journal of Cell Biology, 1997, pp. 1127-1136, vol. 137, No. 5.

R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout.

R&D Systems, Pancreatic Endoderm, Pancreatic Endoderm, Jun. 24, 2013, http://www.rndsystems.com/molecule_group.aspx?g=801 &r, 1 page web printout.

Rajagopal, et al., Insulin Staining of ES Cell Progeny from Insulin Uptake, Science, Jan. 17, 2003, pp. 363, vol. 299.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Ramiya, et al., Reversal of Insulin-Dependent Diabetes Using Islets Generated in vitro from Pancreatic Stem Cells, Nature Medicine, 2000, pp. 278-281, vol. 6.

Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Rebollar, et al., Proliferation of Aligned Mammalian Cells on Laser-Nanostructured Polystyrene, Biomaterials, 2008, pp. 1796-1806, vol. 29.

Reisner, Growing Organs for Transplantation form Embryonic Precursor Tissues, Immunol. Res., 2007, pp. 261-273, vol. 38.

Reubinoff et al., Embryonic stem cell lines from human blastocysts: somatic differentiation in vitro, Nature Biotech, Apr. 18, 2000, pp. 399-404, vol. 18, Nature America Inc.

Rezania, E Al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Rezana, et al., Enrichman of Human Embryonic Stem Cell-Derived NKX6.1-Expressing Pancreatic Progenitor Cells Accelerates the Maturation of Insulin-Secreting Cells In Vivo, Stem Cells, 2013, pp. 2432-2442, vol. 31.

Richards et al., Comparative Evaluation of Various Human Feeders for Prolonged Undifferentiated Growth of Human Embryonic Stem Cells, Stem Cells, 2003, pp. 546-556, vol. 21, AlphaMed Publlishing.

Richards, et al., Development of Defined Media for the Serum-Free Expansion of Primary Keratinocytes and Human Embryonic Stem Cells, Tissue Engineering, 2008, pp. 221-232, vol. 14, No. 3.

Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.

Ricordi et al., Automated Method for Isolation of Human Pancreatic Islets, Diabetes, Apr. 1988, pp. 413-420, vol. 37, American Diabetes Association.

Ross, et al., Cytochrome P450s in the Regulation of Cellular Retinoic Acid Metabolism, Annu. Rev. Nutr., 2011, pp. 65-87. vol. 31.

Rowley, et al., Meeting Lot-Size Challenges of Manufacturing Adherent Cells for Therapy, Cell Therapies Manufacturing, 2012, pp. 16-22, vol. 10, No. 3.

Ryan, et al., Clinical Outcomes and Insulin Secretion After Islet Transplantation with the Edmonton Protocol, Diabetes, Apr. 2001, pp. 710-719, vol. 50.

Sakaguchi, et al., Integration of Adultmesenchymal Stem Cells in the CNS, Society for Neuroscience Abstract Viewer and Itineray Planner, 2002, Program 237.18.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.

Sato, et al., Manipulation of Self-Renewal in Human Embryonic Stem Cells Through a Novel Pharmacological GSK-3 Inhibitor, Methods in Molecular Biology, 2006, pp. 115-128, vol. 331.

Sato, et al., Molecular Signature of Human Embryonic Stem Cells and its Comparison with the Mouse, Developmental Biology, Apr. 23, 2003, pp. 404-413, vol. 260.

Savino et al., Generation of Interleukin-6 Receptor Antagonists by Molecular-Modeling Guided Mutagenesis of Residues Important for gp130 Activation, EMBO Journal, 1994, pp. 1357-1367, vol. 13-6, IT.

Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Schraermeyer, et al., Subretinally Transplanted Embryonic Stem Cells Rescue Photoreceptor Cells From Degeneration in the RCS Rats, Cell Transplantation, 2001, pp. 673-680, vol. 10.

Schroeder, et al., Differentiation of Mouse Embryonic Stem Cells to Insulin-Producing Cells, Nature Protocols, 2005, pp. 495-507, vol. 1, No. 2.

Schuldiner, et al., Induced Neuronal Differentiation of Human Embryonic Stem Cells, Brain Research, 2001, pp. 201-205, vol. 913.

(56) References Cited

OTHER PUBLICATIONS

Schulz, et al., A Scalable System for Production of Functional Pancreatic Progenitors from Human Embryonic Stem Cells, PLOS One, 2012, pp. 1-17, vol. 7, Issue 5.
Scullica, et al., Diagnosis and Classification of Macular Degenerations: an Approach Based on Retinal Function Testing, Documenta Ophthaftnologica, 2001, pp. 237-250, vol. 102.
Seaberg et al., Cfonal identification of multipotent precursors from adult ~ mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-236, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Shi et al., Inducing Embryonic Stem Cells to Differentiate into Pancreatic β Cells by a Novel Three-Step Approach with Activin A and All-Trans Retinoic Acid, Stem Cells, 2005, pp. 656-662, vol. 23, AlphaMed Press.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, pp. 5624-5631, vol. 26, Elsevier.
Shiraki et al., TGF-B Signaling Potentiates Differentiation of Embryonic Stem Cells to Pdx-1 Expressing Endodermal Cells, Genes to Cells, 2005, pp. 503-516, vol. 10, Blackwell Publishing Limited.
Shiraki, et al., Guided Differentiation of Embryonic Stem Cells into Pdx1-Expressing Regional-Specific Definitive Endoderm, Stem Cells, 2006, pp. 874-885, vol. 26.
Sidhu et al., Derivation of Three Clones from Human Embryonic Stem Cell Lines by FACS Sorting and Their Characterization, Stem Cells and Development, 2006, pp. 61-69, vol. 15, Mary Ann Liebert, Inc.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, pp. 749-756, vol. 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, pp. 47-53, vol. 48, Wiley-Liss, Inc.

Sneddon, et al., Self-Renewal of Embryonic-Stem-Cell-Derived Progenitors by Organ-Matched Mesenchyme, Nature, Nov. 29, 2012, pp. 765-770, vol. 491.
Soria et al., Insulin-Secreting Cells Derived From Embryonic Stem Cells Normalize Glycemia in Streptozotocin-Induced Diabetic Mice, Diabetes, Feb. 2000, pp. 1-6, vol. 49, American Diabetes Association.
Soria, et al., From Stem Cells to Beta Cells: New Strategies in Cell Therapy of Diabetes Mellitus, Diabetologia, 2001, pp. 407-415, vol. 44.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precuros Cells, Spinal Motor Neurons and Midbr, Nat Protoc, 2012, pp. 1-26, vol. 6, Issue 8.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Stojkovic et al., An Autogeneic Feeder Cell System That Efficiently Supports Growth of Undifferentiated Human Embryonic Stem Cells, Stem Cells, 2005, pp. 306-314, vol. 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007; pp. 861-872, vol. 131.
Takehara, et al., Rho-Associate Kinase Inhibitor Y-27632 Promotes Survival of Cynomolaus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al,, Chemotherapy with Mitoxantrone Plus Prednisone or Prednisone Alone for Symptomatic Hormone-Resistant Prostate Cancer: A Canadian Randomized Trial Wth Palliative End Points, Journal of Clinical Oncology, 1996, pp. 1756-1764, vol. 14-6, American Society of Clinical Oncology, US.
Teare, et al., Cellular Attachment to Ultraviolet Ozone Modified Polystyrene Surfaces, Langmuir, 2000, pp. 2818-2824, vol. 16.

(56) References Cited

OTHER PUBLICATIONS

Tomita, et al., Bone Marrow-Derived Stem Cells Can Differentiate into Retinal Cells in injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Tulachan et al., TGF-β isoform signaling regulates secondary transition and mesenchymal-induced endocrine development in the embryonic mouse pancreas, Developmental Biology, 2007, pp. 508-521, vol. 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, pp. 28858-28864, vol. 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, pp. 3-9, vol. 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, pp. 961-967, vol. 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 136-142, 480, Elsevier.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, pp. 1221-1227, vol. 23, AlphaMed Press.
Wang et al., Relationship of Chemical Structurs of Anthraquinones with their Effects onthe Suppression of Immune Responses, International Journal of Immunopharmacology, 1987, pp. 733-739, vol. 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, pp. 1104-1108, vol. 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wernig, et al., c-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wiles et al., Embryonic Stem Cell Development in a Chemically Defined Medium, Experimental Cell Research, 1999, pp. 241-248, vol. 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, pp. 972-980, vol. 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang et al., Novel cell immobilization method utilizing centrifugal force to achieve high-density hepatocyte culture in porous scaffold, Journal of Biomed Materials Research, Feb. 27, 2001, pp. 379-386, vol. 55, John Wiley & Sons, Inc.
Yang, et al., Evaluation of Humam MSCs Cell Cycle, Viability and Differentiation in Micromass Culture, Biorheology, 2006, p. 489-496, vol. 43.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Activity, The Journal of Cell Biology, 2005, pp. 443-445, vol. 170, No. 3.

(56) References Cited

OTHER PUBLICATIONS

Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zalzman, et al., Differentiation of Human Liver-Derived, Insulin-Producing Cells Toward the B-Cell Phenotype, Diabetes, 2005, pp. 2568-2575, vol. 54.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, pp. 4969-4976, vol. 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.
Zhang et al., Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, pp. 11887-11894, vol. 280-12, The Amerian Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Zuscik, et al., Regulation of Chondrogenesis and Chondrocyte Differentiation by Stress, J Clin Invest, 2008, pp. 429-438, vol. 118, Issue 2.
Nostro, et al., Generation of Beta Cells from Human Pluripotent Stem Cells: Potential for Regenerative Medicine, Seminars in Cell & Developmental Biology, 2012, pp. 701-710, vol. 23.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Wachs, et al., High Efficacy of Clonal Growth and Expansion of Adult Neural Stem Cells, Laboratory Investigation, 2003, pp. 949-962, vol. 83, No. 7.
Borowiak, et al., How to Make AB Cells, Current Opinion Cell Biology, 2009, pp. 727-732, vol. 21, Issue 6.
Chen, et al., A Small Molecule that Directs Differentiation of Human ESCs into the Pancreatic Lineage, Nature Chemical Biology, Apr. 11, 2009, pp. 258-265, vol. 5, No. 4.
D'Amour et al., Efficient differentiation of human embryonic stem cells to definitive endoderm, Nature Biotechnology, Oct. 28, 2005, pp. 1534-1541, vol. 23, Nature Publishing Group.
Hosoya, et al., Induction of Differentiation of Undifferentiated Cells into Pancreatic Beta-Cells in Vertebrates, Int. J. Dev. Biol., 2012, pp. 313-323, vol. 56.
Konstantinova et al., EphA-Ephrin-A-Mediated Beta Cell Communication Regulates Insulin Secretion from Pancreatic Islets, Cell, Apr. 20, 2007, pp. 359-370, vol. 129.

Loh, et al., Genomic Approaches to Deconstruct Puripotency, Annu Rev Genomics Hum Genet, 2011, pp. 165-185, vol. 12.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Rezania, Production of Functional Glucagon-Secreting-Cells from Human Embryonic Stem Cells, Diabetes, 2011, pp. 239-247, vol. 60, Issue 1.
Sherwood, et al., Transcriptional Dynamics of Endodermal Organ Formation, Developmental Dynamics, 2009, pp. 29-42, vol. 238, Issue 1.
Stafford, et al., Retinoic Acid Signaling is Required for a Critical Early Step in Zebrafish Pancreatic Development, Current Biology, 2002, pp. 1215-1220, vol. 12, Issue 14.
Thomson et al., Embryonic Stem Cell Lines Derived from Human Blastocysts, Science, Nov. 6, 1998, pp. 1145-1147, vol. 282, HighWire Press.
Thomson et al., Isolation of a primate embryonic stem cell line, Developmental Biology, Aug. 1995, pp. 7844-7848, vol. 92, Proc. Natl. Acad. Sci, US.
Wells, et al., Early Mouse Endoderm is Patterned by Soluble Factors from Adjacent Germ Layers, Development, 2000, pp. 1563-1572, vol. 127, Issue 8.
Zorn, et al., Vertebrate Endoderm Development and Organ Formation, Annual Review Cell Development Biology, 2009, pp. 221-251, vol. 25.
Balajthy, et al., Molecular therapies., Molecular therapies, 2011, pp. 1-6, Page Number.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Brimble, S., et al., The Cell Surface Glycosphingolipids SSEA-3 and SSEA-4 Are Not Essential for Human ESC Pluripotency, Stem Cells, Jan. 2007, pp. 54-62, vol. 25.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Chen, et al., Scalable GMP Compliant Suspension Culture System for Human ES Cells, Stem Cell Research, 2012, pp. 388-402, vol. 8.
Cirulli, et al., Netrins: beyond the brain, Molecular Cell Biology, Apr. 2007, pp. 296-306, vol. 8.
Cohick, et al., The Insulin-Like Growth Factors, Annual Reviews Physiol, 1993, pp. 131-153, vol. 55, Annual Reviews Inc.
Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.
Daheron, et al., LIF/STAT3 Signaling Fails to Maintain Self-Renewal of Human Embryonic Stem Cells, Stem Cells, 2004, pp. 770-778, vol. 22.
Findikli, et al., Establishment and characterization of new human embryonic stem cell lines, Reproductive BioMedicine Online, Mar. 3, 2005, pp. 617-627, vol. 10 Issue 5.
Foster, et al., Differentiation of Transplanted Microencapsulated Fetal Pancreatic Cells, Transplantation, Jun. 15, 2007, pp. 1440-1448, vol. 83 Issue 11.
Furue, et al., Heparin promotes the growth of human embryonic stem cells in a defined serum-free medium, PNAS, Sep. 9, 2008, pp. 13409-13414, vol. 105 Issue 36.
Gibco, Insulin-Transferin-Selenium-X 100X; Invitrogen Cell Culture; Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.

(56) References Cited

OTHER PUBLICATIONS

Gordon Weir., Do stem cells hold the key to a future cure for diabetes?, Diabetes Voice, Jun. 2008, pp. 29-31, vol. 53 Issue 2.
Guillemain, et al., Glucose Is Necessary for Embryonic Pancreatic Endocrine Cell Differentiation*, The Journal of Biological Chemistry, May 18, 2007, pp. 15228-15237, vol. 282 Issue 20.
Guo, et al., Efficient differentiation of insulin-producing cells from skin-derived stem cells, Cell Proliferation, 2009, pp. 49-62, vol. 42.
Hebrok, et al., Notochord repression of endodermal Sonic hedgehog permits pancreas development, Genes & Development, Apr. 2, 1998, pp. 1705-1713, vol. 12, Issue 11, Cold Spring Harbor Laboratory Press.
Hiemisch, H., et al., Transcriptional Regulation in Endoderm Development: Characterization of an Enhancer Controlling Hnf3g Expression by Transgenesis and Targeted Mutagenesis, The EMBO Journal, 1997, 3995-4006, vol. 16(13).
Jaenisch, et al., Stem Cells, the Molecular Circuitry of Pluripotency and Nuclear Reprogramming, cell, Feb. 22, 2008, pp. 567-582, vol. 132, Elsevier Inc.
Jean, et al., Pluripotent genes in avian stem cells, Development Growth & Differentiation, 2013, pp. 41-51, vol. 55.
Kang, et al., Plasma treatment of textiles—Synthetic Polymer—Based Textiles, AATCC Review, 2004, pp. 29-33, Page number.
Kehoe, et al., Scalable Stirred-Suspension Bioreactor Culture of Human Pluripotent Stem Cells, Tissue Eng Part A, 2010, pp. 405-421, vol. 16 Issue 2.
Kim, et al,. Reprogrammed Pluripotent Stem Cells from Somatic Cells, International Journal of Stem Cells, 2011, pp. 1-8, vol. 4 Issue 1.
King, et al., Bioreactor development for stem cell expansion and controlled differentiation, Current Opinion in Chemical Biology, Jul. 25, 2007, pp. 394-398, vol. 11, Elsevier Ltd.
Klajnert, et al., Fluorescence studies on PAMAM dendrimers interactions with bovine serum albumin, Bioelectrochemistry, 2002, pp. 33-35, vol. 55.
Kubota,et al., Growth factors essential for self-renewal and expansion of mouse spermatogonial stem cells, cell Biology, Nov. 23, 2004, pp. 16489-16494, vol. 101, Issue 47.
Kunisada, et al., Small molecules induce efficient differentiation into insulin-producing cells from human induced pluripotent stem cells, Stem Cell Research, Oct. 11, 2011, pp. 274-284, vol. 8.
Lavial, et al., Chicken Embryonic Stem Cells as a Non-Mammalian Embryonic Stem Cell Model, Development Growth Differentiation, Jan. 2010, pp. 101-114, vol. 52(1).
Lee, et al., Available human feeder cells for the maintenance of human embryonic stem cells, Reproduction, 2004, pp. 727-735, vol. 128.
Lin, C., et al., Coagulation Dysregulatin as a Barrier to Xenotransplantation n the Primate, Transplant Immunology, 2009, pp. 75-80, vol. 21.
Ludwig, et al., Defined, Feeder-Independent Medium for human Embryonic Stem Cell Culture, Current Protocols in Stem Cell Biology, 2007, pp. 1C.2.1-1C.2.16, vol. 1, John Wiley & Sons, Inc.
Maimets, et al., Activation of p53 by nuntlin leads to rapid differentiation of human embryonic stem cells, Oncogene, Jun. 2, 2008, pp. 5277-5287, vol. 27.
Maria-Jesus Obregon, Thyroid hormone and adipocyte differentiation, Thyroid, 2008, pp. 185-195, vol. 18 Issue 2.
McMahon, et al., Noggin-mediated antagonism of BMP signaling is required for growth and patterning of the neural tube and somite, Genes & Development, Mar. 16, 1998, pp. 1438-1452, vol. 12.
Micallef, et al., Pancreas Differentiation of Mouse ES Cells, Embryonic and Extraembryonic Stem Cells, 2007, pp. 1-8, Supplementary 2.
Misiti, et al., 3.5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.
Nakanishi, et al., Pancreatic tissue formation from murine embryonic stem cells in vitro, Differentiation, 2007, pp. 1-11, vol. 75.

Nakase, et al., Myeliod Antigen, CD13, CD14, and/ or CD33 Expression Is Restricted to Certain Lymphoid Neoplasms, Hematopathology, Jun. 1996, pp. 761-768, vol. 105 Issue 6.
Narang, A., et al., Biological and Biomaterial Approaches for Improved Islet Transplantation, Pharmacological Review, Jun. 2006, pp. 194-243, vol. 58(2).
Nekrasov, et al., Induced pluripotent stem cells as a model for studying human diseases, Cellular Transplantology and Tissue Engineering, 2011, pp. 32-37, vol. 6 Issue 2.
Olmer, et al., Long Term Expansion of Undifferentiated Human iPS and ES Cells in Suspension Culture Using Defined Medium, Stem Cell Research, 2010, pp. 51-64, vol. 5.
Osafune, et al., Marked differences in differentiation propensity among human embryonic stem cell lines, Nature Biotechnology, Feb. 17, 2008, pp. 313-315, vol. 26 Issue 3.
Ouziel-Yahalom, et al., Expansion and redifferentiation of adult human pancreatic islet cells, Biochemical and Biophysical Research Communications, Jan. 19, 2006, pp. 291-298, vol. 341.
Petitte, J., et al., Avian Pluripotent Stem Cells, Mechanisms of Development, 2004, pp. 1159-1168, vol. 121.
Ramiya, et al., Reversal of insulin-dependent diabetes using islets generated in vitro from pancreatic stem cells, Nature Medicine, Mar. 2000, pp. 278-282, vol. 6 Issue 3.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytochemistry, 1986, pp. 527-533, vol. 34, Issue 4.
Rother, et al., Challenges facing islet transplantation for the treatment of type 1 diabetes mellitus, The Journal of Clinical Investigation, 2004, pp. 677-863, vol. 114 Issue 7.
Rowely, et al., Meeting Lot-size Challenges of Manufacturing Adherent Cells for Therapy, Bio Process International, Mar. 2012, pp. 16-22, vol. 10 Issue 3.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.
Sigma-Aldrich, Sigma-Aldrich Inc., Sigma-Aldrich, 2007, pp. 1-2, page number.
Sjo''gren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
Thomson, Bioprocessing of Embryonic Stem Cells for Drug Discovery, Trends in Biotechnology, 2007, pp. 224-230, vol. 25, No. 5.
Verkhovskaya, et al., Effect of alkoxy-substituted of glycerin on the morphofunctional properties of continuous cell culture, Cryobiology, 1990, pp. 30-33, vol. 1.
Wang, et al., Cultivation and identification of pancreatic endocrine progenitor cells, National Medical Journal of China, 2006, pp. 1850-1853, vol. 86 Issue 26.
Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.
Yadlin, et al., Small-molecule inducers of insulin expression in pancreatic α-cells, PNAS, Aug. 24, 2010, pp. 15099-15104, vol. 107 Issue 34.
Yang JW, et al., Evaluation of human MSCs cell cycle, viability and differentiation in micromass culture, Biorheology, 2006, pp. 1-2, vol. 43 Issue (3-4).
Yim,et al., Proliferation and differentiation of human embryonic germ cell derivatives in bioactive polymeric fibrous scaffold, J.Biomater. Sci.Polymer Edn., Jan. 19, 2005, pp. 1193-1217, vol. 16 Issue 10.

(56) References Cited

OTHER PUBLICATIONS

Zhu, et al., A Small Molecule Primes Embryonic Stem Cells for Differentiation, Cell Stem Cell, May 8, 2009, pp. 416-426, vol. 4.

Zulewski, et al., Multipotentital Nestin-Positive Stem Cells Isolated From Adult Pancreatic Islets Differentiate Ex Vivo Into Pancreatic Endocrine, Exocrine, and Hepatic Phenotypes, Diabetes, 2001, pp. 521-533, vol. 50.

Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.

* cited by examiner

Control

+ 50 ng/ml Ephrin A3

+100 ng/ml Ephrin A3

Control

+50 ng/ml Ephrin A4

+100 ng/ml Ephrin A4

S6 1D

S6 7D

S6 10D

S6 10D

Hb9

NKX6.1

Insulin

Hb9

S6 3D (10X)

S6 3D (20X)

NKX6.1+
Epithelial cord

Endocrine
clusters

DIFFERENTIATION OF HUMAN EMBRYONIC STEM CELLS INTO PANCREATIC ENDOCRINE CELLS

CROSS REFERENCE TO RELATED APPLICATION

The present application is a divisional of U.S. Ser. No. 13/911,829, filed Jun. 6, 2013, which claims the benefit of U.S. Provisional Patent Application Ser. No. 61/657,160, filed Jun. 8, 2012, both of which are incorporated herein by reference in their entirety.

FIELD OF THE INVENTION

The present invention is in the field of cell differentiation. More specifically, the invention discloses use of Ephrin ligands and sphingosine-1-phosphate as regulators of differentiation of pluripotent stem cells to endocrine cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. The intermediate stage in this process is the formation of definitive endoderm. Definitive endoderm cells express a number of markers, such as, HNF3beta, GATA4, MIXL1, CXCR4 and SOX17.

By the end of gastrulation, the endoderm is partitioned into anterior-posterior domains that can be recognized by the expression of a panel of factors that uniquely mark anterior, mid, and posterior regions of the endoderm. For example, Hhex, and Sox2 identify the anterior region while Cdx1, 2, and 4 identify the posterior half of the endoderm.

Migration of endoderm tissue brings the endoderm into close proximity with different mesodermal tissues that help in regionalization of the gut tube. This is accomplished by a plethora of secreted factors, such as FGFs, Wnts, TGF-Bs, retinoic acid (RA), and BMP ligands and their antagonists. For example, FGF4 and BMP promote Cdx2 expression in the presumptive hindgut endoderm and repress expression of the anterior genes Hhex and SOX2 (2000 Development, 127:1563-1567). WNT signaling has also been shown to work in parallel to FGF signaling to promote hindgut development and inhibit foregut fate (2007 Development, 134:2207-2217). Lastly, secreted retinoic acid by mesenchyme regulates the foregut-hindgut boundary (2002 Curr Biol, 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. For example, the regionalized pancreas domain in the gut tube shows a very high expression of PDX1 and very low expression of CDX2 and SOX2. Similarly, the presence of high levels of Foxe1 are indicative of esophagus tissue; highly expressed in the lung tissue is NKX2.1; SOX2/Odd1 (OSR1) are highly expressed in stomach tissue; expression of PROX1/Hhex/AFP is high in liver tissue; SOX17 is highly expressed in biliary structure tissues; PDX1, NKX6.1/PTf1a, and NKX2.2 are highly expressed in pancreatic tissue; and expression of CDX2 is high in intestine tissue. The summary above is adapted from Dev Dyn 2009, 238:29-42 and Annu Rev Cell Dev Biol 2009, 25:221-251.

Formation of the pancreas arises from the differentiation of definitive endoderm into pancreatic endoderm (2009 Annu Rev Cell Dev Biol, 25:221-251; 2009 Dev Dyn, 238:29-42). Dorsal and ventral pancreatic domains arise from the foregut epithelium. Foregut also gives rise to the esophagus, trachea, lungs, thyroid, stomach, liver, pancreas, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

D'Amour et al. describes the production of enriched cultures of human embryonic stem (ES) cell-derived definitive endoderm in the presence of a high concentration of activin and low serum (Nature Biotechnol 2005, 23:1534-1541; U.S. Pat. No. 7,704,738). Transplanting these cells under the kidney capsule of mice resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF-10 and retinoic acid (U.S. Patent Publication No. 2005/0266554A1). Subsequent transplantation of these pancreatic precursor cells in the fat pad of immune deficient mice resulted in formation of functional pancreatic endocrine cells following a 3-4 month maturation phase (U.S. Pat. No. 7,993,920 and U.S. Pat. No. 7,534,608).

Fisk et al. report a system for producing pancreatic islet cells from human embryonic stem cells (U.S. Pat. No. 7,033,831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-B receptor and BMP receptors (Development 2011, 138:861-871; Diabetes 2011, 60:239-247) have been used to significantly enhance number of pancreatic endocrine cells. In addition, small molecule activators have also been used to generate definitive endoderm cells or pancreatic precursor cells (Curr Opin Cell Biol 2009, 21:727-732; Nature Chem Biol 2009, 5:258-265).

Although great strides have been made in improving protocols to generate pancreatic cells from human pluripotent stem cells, there is still a need to generate a protocol that results in functional endocrine cells and in particular beta cells. Here, we demonstrate that a class of Ephrin ligands and sphingosine-1-phosphate or agonists of sphingosine receptor enhance production of endocrine cells and accelerate clustering of endocrine hormones and endocrine precursor cells.

SUMMARY

In an embodiment, the present invention relates to a method of enhancing expression of insulin and NKX6.1 by culturing a population of pancreatic endoderm cells in medium comprising Ephrin A4 or Ephrin A3. In some embodiments, the population of pancreatic endoderm cells do not substantially express CDX2 or SOX2. In some embodiments, the population pancreatic endoderm cells are obtained by a stepwise differentiation of pluripotent cells. In some embodiments, the pluripotent cells are human embryonic pluripotent cells.

In an embodiment, the invention concerns a method of enhancing expression of somatostatin while suppressing the expression of insulin, glucagon, and ghrelin by culturing pancreatic endoderm cells in medium comprising Activin A or Activin C. In some embodiments, the population of pancreatic endoderm cells treated with Activin A or Activin C expresses more somatostatin as a population of pancreatic endoderm cells non-treated with Activin A or Activin C. In some embodiments, the expression of insulin is suppressed in the population of pancreatic endoderm cells treated with Activin A or Activin C as compared to the expression of insulin in a population of pancreatic endoderm cells non-treated with Activin A or Activin C. In some embodiments, the expression of glucagon in the population of pancreatic endoderm cells treated with Activin A or Activin C is suppressed as compared to the expression of glucagon in a population of pancreatic endoderm cells non-treated with Activin A or Activin C. In some embodiments, the expression of ghrelin is suppressed in the population of pancreatic endoderm cells treated with Activin A or Activin C as compared to the expression of ghrelin in a population of pancreatic endoderm cells non-treated with Activin A or Activin C. In some embodiments, the pancreatic endoderm cells do not substantially express CDX2 or SOX2. In some embodiments, the pancreatic endoderm cells treated with Activin A or Activin C are obtained by a stepwise differentiation of pluripotent cells. In some embodiments, the pluripotent cells where the pancreatic endoderm cells are derived from are human embryonic pluripotent cells.

In an embodiment, the invention refers to a method of enhancing expression of NKX6.1 by treating pancreatic endoderm cells in medium comprising semaphorin 3a or Epigen. In some embodiments, the population of pancreatic endoderm cells treated with medium comprising semaphorin 3a or Epigen expresses an enhanced amount of NKX6.1 as compared to pancreatic endoderm cells non-treated with medium comprising semaphorin 3a or Epigen. In some embodiments, the level of expression of hormones such as insulin, glucagon, and gherlin is not affected in pancreatic endoderm cells treated with medium comprising semaphorin 3a or Epigen as compared to pancreatic endoderm cells not treated with medium comprising semaphorin 3a or Epigen. In some embodiments, the pancreatic endoderm cells do not substantially express CDX2 or SOX2. In some embodiments, the pancreatic endoderm cells treated with medium comprising semaphorin 3a or Epigen are obtained by a stepwise differentiation of pluripotent cells. In some embodiments, the pluripotent cells where the pancreatic endoderm cells are derived from are human embryonic pluripotent cells.

In some embodiments, the present invention relates to a stepwise method of differentiating pluripotent cells comprising culturing pancreatic endoderm cells in medium comprising Ephrin A4, Ephrin A3, Activin A, Activin C, semaphorin 3a, or Epigen. In some embodiments, the pancreatic endoderm cells are cultured in medium comprising Ephrin A4 or Ephrin A3. In some embodiments, the pancreatic endoderm cells are cultured in medium comprising Activin A or Activin C. In some embodiments, the pancreatic endoderm cells are cultured in medium comprising semaphorin 3a, or Epigen. In some embodiments, the pluripotent stem cells where the pancreatic endoderm cells are derived from are human embryonic pluripotent stem cells.

In an embodiment, the present invention relates to a method of inducing expression of endocrine clusters by treating pancreatic endocrine cells with sphingosine-1 receptor agonist. In some embodiments, the sphingosine-1 receptor agonist used for treating pancreatic endocrine cells is sphingosine-1-phosphate (S1P)

Also contemplated as embodiments of the invention are cells prepared by the methods of the invention, and methods of using the cells of the invention.

BRIEF DESCRIPTION OF THE DRAWINGS

FIG. 2A, control; FIG. 2B, cells treated with 50 ng/ml Ephrin-A3; and FIG. 2C, cells treated with 100 ng/ml Ephrin-A3, as described in Example 2.

FIG. 3A, control; FIG. 3B, cells treated with 50 ng/ml Ephrin-A4; and FIG. 3C, cells treated with 100 ng/ml Ephrin-A4, as described in Example 2.

FIG. 6C, control cells; FIG. 6D, cells treated with S1P.

DETAILED DESCRIPTION

Figure 1A:
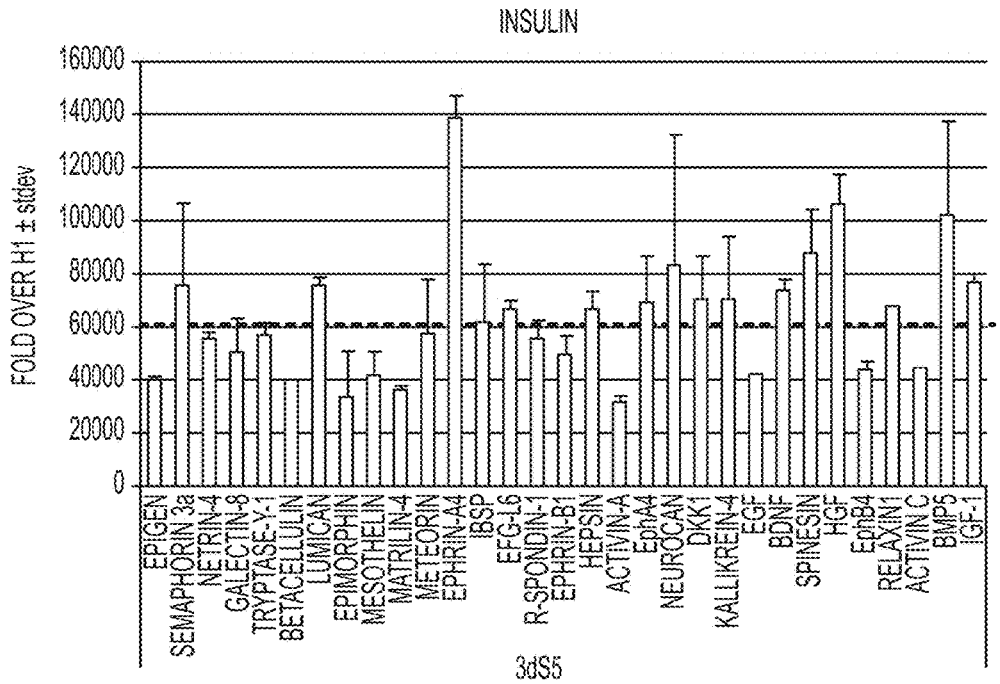
FIG. 1A to FIG. 1G shows data from real-time PCR analyses of the expression of the following genes in cells of the human embryonic stem cell line H1 differentiated as described in Example 1: insulin (FIG. 1A), somatostatin (FIG. 1B), ghrelin (FIG. 1C), glucagon (FIG. 1D), PDX1 (FIG. 1E), NKX6.1 (FIG. 1F), and NGN3 (FIG. 1G).
Figure 1B:
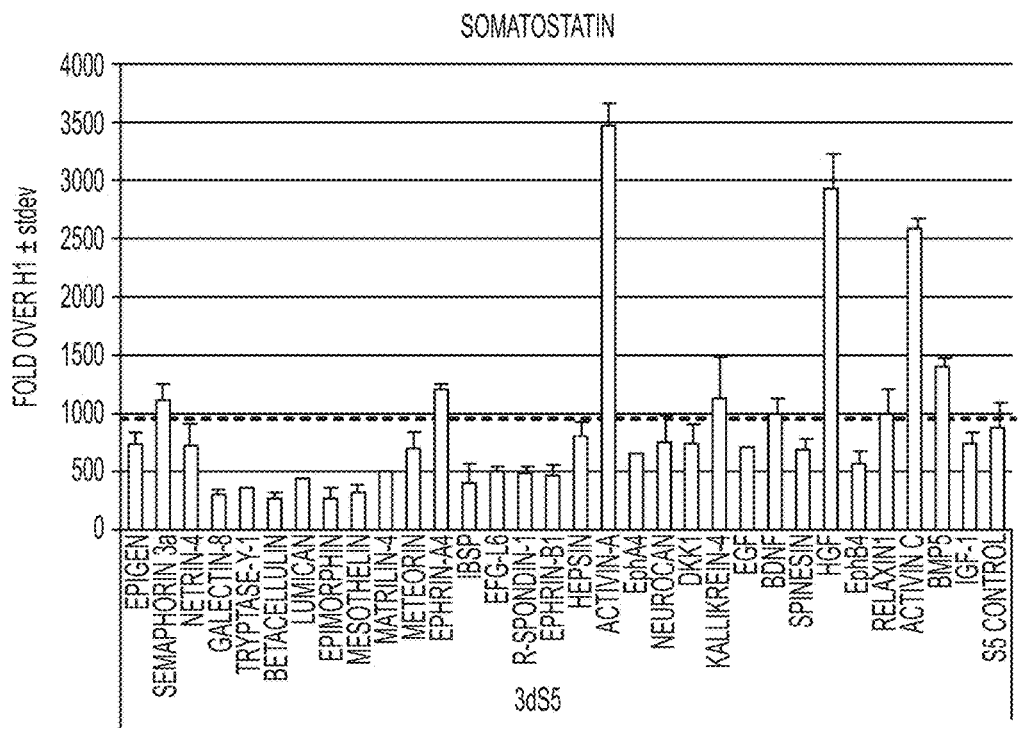
Figure 1C:
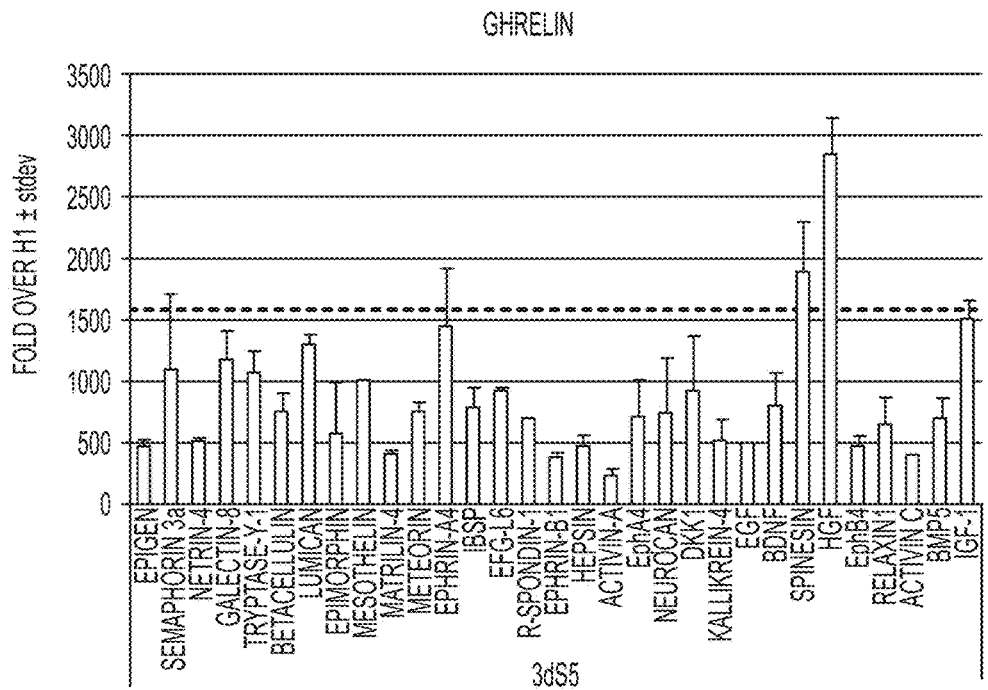
Figure 1D:
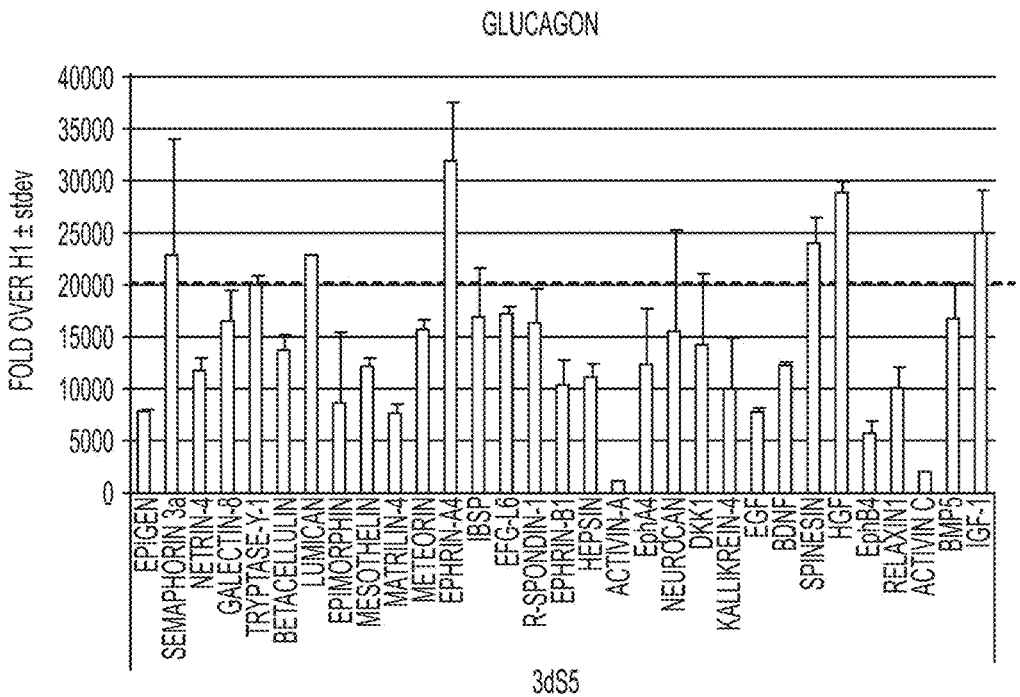
Figure 1E:
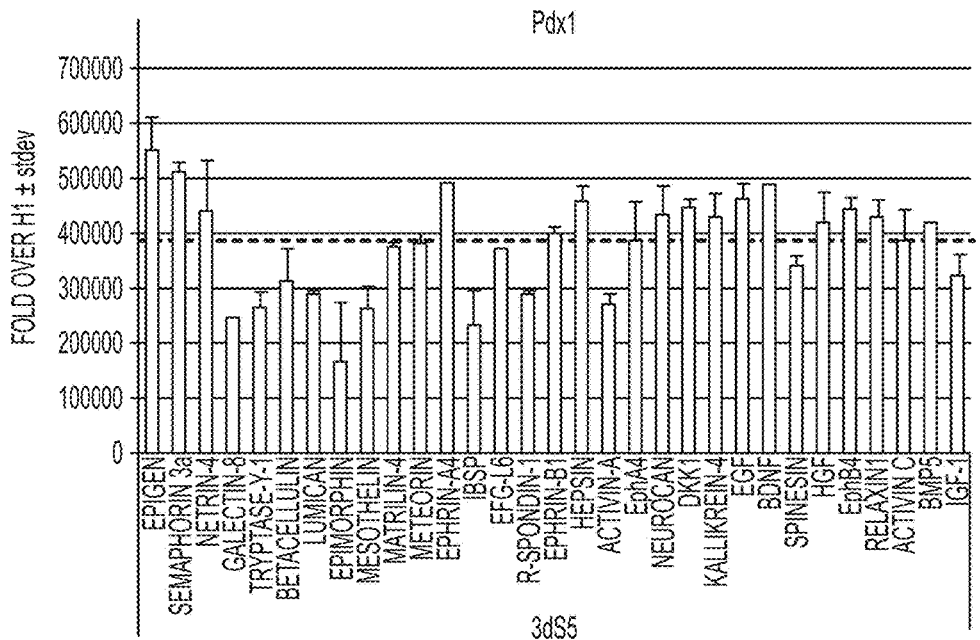
Figure 1F:
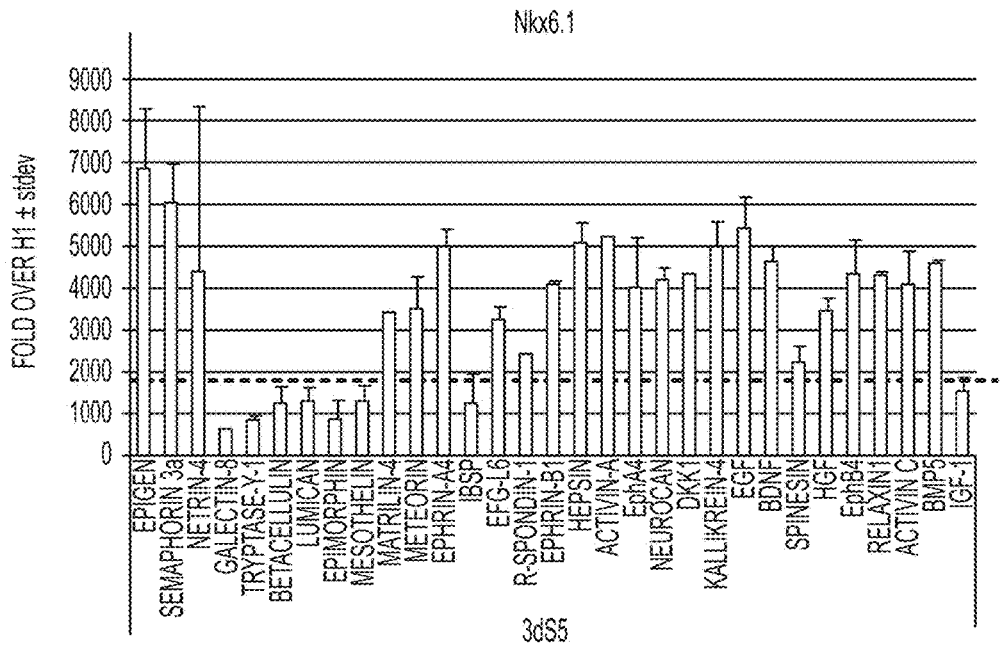

For clarity of disclosure, and not by way of limitation, the detailed description of the invention is divided into the following subsections that describe or illustrate certain features, embodiments or applications of the present invention.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm). Stem cells also give rise to tissues of multiple germ layers following transplantation and contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated cell or a differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is detected in the cell. Similarly, the cell is "negative for" a specific marker, or "negative" when the specific marker is not detected in the cell.

As used herein, "Cell density" and "Seeding Density" are used interchangeably herein and refer to the number of cells seeded per unit area of a solid or semisolid planar or curved substrate.

As used herein, "stage 1" and "S1" are used interchangeably to identify cells expressing markers characteristic of the definitive endoderm (DE).

"Definitive endoderm", as used herein, refers to cells which bear the characteristics of cells arising from the epiblast during gastrulation and which form the gastrointestinal tract and its derivatives. Definitive endoderm cells express at least one of the following markers: HNF3 beta, GATA4, SOX17, CXCR4, Cerberus, OTX2, goosecoid, C-Kit, CD99, and MIXL1.

"Gut tube", as used herein, refers to cells derived from definitive endoderm that express at least one of the following markers: HNF3-beta, HNF1-beta, or HNF4-alpha. Gut tube cells can give rise to all endodermal organs, such as lungs, liver, pancreas, stomach, and intestine.

Used herein interchangeably are "stage 2" and "S2" which identify cells expressing markers characteristic of the primitive gut tube.

"Foregut endoderm" refers to endoderm cells that give rise to esophagus, lungs, stomach, liver, pancreas, gall bladder, and a portion of the duodenum.

"Posterior foregut" refers to endoderm cells that can give rise to posterior stomach, pancreas, liver, and a portion of the duodenum.

"Mid-gut endoderm" refers to endoderm cells that can give rise to the intestines, portions of the duodenum, appendix, and ascending colon.

"Hind-gut endoderm" refers to endoderm cells that can give rise to the distal third of the transverse colon, the descending colon, sigmoid colon and rectum.

Both "stage 3" and "S3" are used interchangeably to identify cells expressing markers characteristic of the foregut endoderm. "Cells expressing markers characteristic of the foregut lineage", as used herein, refers to cells expressing at least one of the following markers: PDX1, FOXA2, CDX2, SOX2, and HNF4 alpha.

Used interchangeably herein are "stage 4" and "S4" to identify cells expressing markers characteristic of the pancreatic foregut precursor. "Cells expressing markers characteristic of the pancreatic foregut precursor lineage", as used herein, refers to cells expressing at least one of the following markers: PDX1, NKX6.1, HNF6, FOXA2, PTF1a, Prox1 and HNF4 alpha.

As used herein, "stage 5" and "S5" are used interchangeably to identify cells expressing markers characteristic of the pancreatic endoderm and pancreatic endocrine precursor cells. "Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage do not substantially express CDX2 or SOX2.

"Pancreatic endocrine cell", or "Pancreatic hormone expressing cell", or "Cells expressing markers characteristic of the pancreatic endocrine lineage", or "Stage 6 cells", or "S6 cells" are used interchangeably herein, and refer to a cell capable of expressing at least one of the following hormones: insulin, glucagon, somatostatin, ghrelin, and pancreatic polypeptide.

"Pancreatic insulin positive cell" refers to an endocrine population of cells expressing insulin, HB9, NKX2.2 and NKX6.1.

"Pancreatic endocrine precursor cell" or "Pancreatic endocrine progenitor cell" refers to pancreatic endoderm cells capable of becoming a pancreatic hormone expressing cell. Such a cell can express at least one of the following markers: NGN3, NKX2.2, NeuroD, ISL-1, Pax4, Pax6, or ARX.

Used interchangeably herein are "d1", "d 1", and "day 1"; "d2", "d 2", and "day 2"; "d3", "d 3", and "day 3", and so on. These number letter combinations refer to a specific day of incubation in the different stages during the stepwise differentiation protocol of the instant application.

"Glucose" and "D-Glucose" are used interchangeably herein and refer to dextrose, a sugar commonly found in nature.

Used interchangeably herein are "NeuroD" and "NeuroD 1" which identify a protein expressed in pancreatic endocrine progenitor cells and the gene encoding it.

Used interchangeably herein are "LDN" and "LDN-193189" to indicate a BMP receptor inhibitor available from Stemgent, Calif., USA.

Isolation, Expansion and Culture of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al. 1998, Science 282:1145-1147). Differentiation of pluripotent stem cells in vitro results in the loss of SSEA-4, Tra-1-60, and Tra-1-81 expression. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, CA, USA). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into SCID mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered. Pluripotent cells may be readily expanded in culture using various feeder layers or by using matrix protein coated vessels. Alternatively, chemically defined surfaces in combination with defined media such as mTesr®1 media (StemCell Technologies, Vancouver, Canada) may be used for routine expansion of the cells. Pluripotent cells may be readily removed from culture plates using enzymatic, mechanical or use of various calcium chelators such as EDTA (Ethylenediaminetetraacetic acid). Alternatively, pluripotent cells may be expanded in suspension in the absence of any matrix proteins or a feeder layer.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells (hESCs) or human embryonic germ cells, such as, for example the human embryonic stem cell lines H1, H7, and H9 (WiCell Research Institute, Madison, Wis., USA). Also suitable are cells taken from a pluripotent stem cell population already cultured in the absence of feeder cells. Also suitable are inducible pluripotent cells (IPS) or reprogrammed pluripotent cells that can be derived from adult somatic cells using forced expression of a number of pluripotent related transcription factors, such as OCT4, NANOG, Sox2, KLF4, and ZFP42 (Annu Rev Genomics Hum Genet 2011, 12:165-185). The human embryonic stem cells used in the methods of the invention may also be prepared as described by Thomson et al. (U.S. Pat. No. 5,843,780; Science, 1998, 282:1145-1147; Curr Top Dev Biol 1998, 38:133-165; Proc Natl Acad Sci U.S.A. 1995, 92:7844-7848).

Formation of Cells Expressing Markers Characteristic of the Pancreatic Endoderm Lineage from Pluripotent Stem Cells Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, Tra 1-60, Tra 1-81.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell wherein the expression of PDX1 and NKX6.1 are substantially higher than the expression of CDX2 and SOX2.

Markers characteristic of the pancreatic endocrine lineage are selected from the group consisting of NGN3, NEUROD, ISL1, PDX1, NKX6.1, PAX4, ARX, NKX2.2, and PAX6. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

The pancreatic endocrine cells of the invention are cells expressing markers characteristic of the β cell lineage. A cell expressing markers characteristic of the β cell lineage expresses PDX1 and at least one of the following transcription factors: NKX2.2, NKX6.1, NEUROD, ISL1, HNF3 beta, MAFA, PAX4, and PAX6. In one aspect of the present invention, a cell expressing markers characteristic of the β cell lineage is a β cell.

In an embodiment, the present invention relates to a method of enhancing expression of insulin and NKX6.1 by culturing a population of stage 5 cells in medium comprising Ephrin A4 or Ephrin A3. In some embodiments, the expression of insulin and NKX6.1 is enhanced in the population of cells to at least 2 times as much as the expression of insulin and NKX6.1 in a population of non-treated cells. In some embodiments, the population of stage 5 cells do not substantially express CDX2 or SOX2. In some embodiments, the population stage 5 cells are obtained by a stepwise differentiation of pluripotent cells. In some embodiments, the pluripotent cells are human embryonic pluripotent cells.

In an embodiment, the invention concerns a method of enhancing expression of somatostatin while suppressing the expression of insulin, glucagon, and ghrelin by culturing stage 5 cells in medium comprising Activin A or Activin C. In some embodiments, the treated population of cells expresses at least two times as much somatostatin as non-treated cultures. In some embodiments, the expression of insulin is suppressed to about half as much as the expression of insulin in non-treated cultures. In some embodiments, the expression of glucagon is suppressed to about 1/10 as much as the expression of glucagon in non-treated cultures. In some embodiments, the expression of ghrelin is suppressed to about 1/3 as much as the expression of ghrelin as in non-treated cultures. In some embodiments, the stage 5 cells do not substantially express CDX2 or SOX2. In some embodiments, the stage 5 cells are obtained by a stepwise differentiation of pluripotent cells. In some embodiments, the pluripotent cells are human embryonic pluripotent cells.

In an embodiment, the invention refers to a method of enhancing expression of NKX6.1 by treating stage 5 cells in medium comprising semaphorin 3a or Epigen. In some embodiments, the treated population of cells expresses at least two times as much NKX6.1 as non-treated cultures. In some embodiments, the level of expression of hormones is not affected in treated cultures as compared to untreated cultures. In some embodiments, the stage 5 cells do not substantially express CDX2 or SOX2. In some embodiments, the stage 5 cells are obtained by a stepwise differentiation of pluripotent cells. In some embodiments, the pluripotent cells are human embryonic pluripotent cells.

In some embodiments, the present invention relates to a stepwise method of differentiating pluripotent cells comprising culturing stage 5 cells in medium comprising Ephrin A4, Ephrin A3, Activin A, Activin C, semaphorin 3a, or Epigen. In some embodiments, the stage 5 cells are cultured in medium comprising Ephrin A4 or Ephrin A3. In some embodiments, the stage 5 cells are cultured in medium comprising Activin A or Activin C. In some embodiments, the stage 5 cells are cultured in medium comprising semaphorin 3a, or Epigen. In some embodiments, the pluripotent stem cells are human embryonic pluripotent stem cells.

In an embodiment, the invention relates to a method of inducing insulin expression comprising culturing pancreatic endoderm cells with an Ephrin ligand. In some embodiments, the Ephrin ligand is selected from Ephrin A3 and Ephrin A4. In some embodiments, culturing the pancreatic endoderm cells with an Ephrin ligand enhances expression of insulin and NKX6.1. In some embodiments, culturing the pancreatic endoderm cells with an Ephrin ligand enhances expression of insulin and NKX6.1 in the pancreatic endoderm cells to at least 2 times as much as the expression of insulin and NKX6.1 in non-treated pancreatic endoderm cells. In some embodiments, the pancreatic endoderm cells do not substantially express CDX2 or SOX2. In some embodiments, the pancreatic endoderm cells are obtained by a stepwise differentiation of pluripotent stem cells. In some embodiments, the pluripotent stem cells used in the methods of the invention are human embryonic pluripotent stem cells.

In an embodiment, the invention concerns insulin and NKX6.1-expressing cells prepared by the methods of the invention.

In an embodiment, the invention refers to a method for inducing endocrine cluster formation comprising culturing pancreatic endoderm cells with a sphingosine-1 receptor agonist. In some embodiments, the pancreatic endoderm cells are obtained by a stepwise differentiation of pluripotent stem cells. In some embodiments, the pluripotent stem cells are human embryonic pluripotent stem cells.

Publications cited throughout this document are hereby incorporated by reference in their entirety. The present invention is further illustrated, but not limited, by the following examples.

EXAMPLES

Example 1

Identification of EphrinA4 as a Strong Inducer of Insulin Expression

This example was carried out to understand the role of various proteins on the generation of pancreatic endoderm/endocrine cultures from the differentiation of human ES cells.

Cells of the human embryonic stem cell line H1 (hESC H1, passage 40) were seeded as single cells at $1\times10^5$ cells/cm$^2$ on MATRIGEL™ (1:30 dilution; BD Biosciences, NJ)-coated dishes in mTeSR®1 media (StemCell Technologies, Vancouver, Canada) supplemented with 10 µM of Y27632 (Rock inhibitor, Catalog No. Y0503, SigmaAldrich, St. Louis, Mo.). Forty-eight hours post seeding, cultures were washed in incomplete PBS (phosphate buffered saline without Mg or Ca). Cultures were differentiated into pancreatic endoderm/endocrine lineages as follows:

a) Stage 1 (Definitive Endoderm (DE)—3 days): Cells were cultured for one day in stage 1 media: MCDB-131 medium (Catalog No. 10372-019, Invitrogen, Carlsbad, Calif.) supplemented with 0.1% fatty acid-free BSA (Catalog No. 68700, Proliant, Ankeny, Iowa), 0.0012 g/ml sodium bicarbonate (Catalog No. S3187, SigmaAldrich, St. Louis, Mo.), 1× GlutaMax™ (Invitrogen Catalog No. 35050-079), 4.5 mM D-Glucose (SigmaAldrich Catalog No. G8769), 100 ng/ml GDF8 (R&D Systems, Minneapolis, Minn.) and 1 µM MCX compound (a GSK3B inhibitor, 14-Prop-2-en-1-yl-3,5,7,14,17,23,27-heptaazatetracyclo [19.3.1.1~2,6~0.1~8,12~]heptacosa-1(25),2(27),3,5,8(26),9,11,21,23-nonaen-16-one, US Patent Application Publication No. 2010-0015711; incorporated herein by reference in its entirety). Cells were then cultured for additional day in MCDB-131 medium supplemented with 0.1% fatty acid-free BSA, 0.0012 g/ml sodium bicarbonate, 1× GlutaMax™, 4.5 mM D-Glucose, 100 ng/ml GDF8, and 0.1 µM MCX compound. Cells were then cultured for an additional day in MCDB-131 medium supplemented with 0.1% fatty acid-free BSA, 0.0012 g/ml sodium bicarbonate, 1× GlutaMax™, 4.5 mM D-Glucose, and 100 ng/ml GDF8, then b) Stage 2 (Primitive gut tube—2 days): Cells were treated for two days with MCDB-131 medium supplemented with 0.1% fatty acid-free BSA; 0.0012 g/ml sodium bicarbonate; 1× GlutaMax™; 4.5 mM D-Glucose; 0.25 mM ascorbic acid (Sigma, St. Louis, Mo.) and 25 ng/ml FGF7 (R & D Systems, Minneapolis, Minn.), then c) Stage 3 (Foregut—2 days): Cells were treated with MCDB-131 medium supplemented with a 1:200 dilution of ITS-X (Invitrogen); 4.5 mM Glucose; 1× GlutaMax™; 0.0017 g/ml sodium bicarbonate; 2% fatty acid-free BSA; 0.25 µM SANT-1 (Sigma, St. Louis, Mo.); 10 ng/ml of Activin-A (R & D Systems); 1 µM retinoic acid (RA; Sigma); 25 ng/ml FGF7; 0.25 mM ascorbic acid; 200 nM TPB (a PKC activator; Catalog No. 565740; EMD Chemicals, Gibstown, N.J.); 10 µM forskolin (FSK, Sigma), and 100 nM LDN (a BMP receptor inhibitor; Catalog No. 04-0019; Stemgent; San Diego, Calif.) for day 1. On day 2, cells were treated with MCDB-131 medium supplemented with a 1:200 dilution of ITS-X; 4.5 mM Glucose; 1× GlutaMax™; 0.0017 g/ml sodium bicarbonate; 2% fatty acid-free BSA; 0.25 µM SANT-1; 10 ng/ml of Activin A; 1 µM RA; 25 ng/ml FGF7; 0.25 mM ascorbic acid, 200 nM TPB, 10 µM forskolin and 10 nM LDN, then d) Stage 4 (Pancreatic foregut precursor—2 days): Cells were treated with MCDB-131 medium supplemented with a 1:200 dilution of ITS-X; 4.5 mM Glucose; 1× GlutaMax™; 0.0015 g/ml sodium bicarbonate; 2% fatty acid-free BSA; 0.25 µM SANT-1; 50 nM RA; 50 nM LDN-193189; 10 µM forskolin; 0.25 mM ascorbic acid; and 100 nM TPB for two days, then e) Stage 5 (Pancreatic endoderm/endocrine—3 days): Stage 4 cells were treated with MCDB-131 medium supplemented with a 1:200 dilution of ITS-X; 20 mM Glucose; 1× GlutaMax™; 0.0015 g/ml sodium bicarbonate; 2% fatty acid-free BSA; 0.25 µM SANT-1; 50 nM RA; 10 µM forskolin; 0.25 mM ascorbic acid for three days, with the addition of 100 nM ALk5 inhibitor SD-208 (disclosed in Molecular Pharmacology 2007, 72:152-161) for days 2-3 only.

At day 1 of stage 5, the factors listed in Table I, below, were spiked into the media and upon completion of S5 (day 3 of stage 5) mRNA was collected for PCR analysis of relevant pancreatic endoderm/endocrine genes. As a control, cultures were treated only with the S5 media listed above. Total RNA was extracted with the RNeasy Mini Kit (Qiagen; Valencia, Calif.) and reverse-transcribed using a High Capacity cDNA Reverse Transcription Kit (Applied Biosystems, Foster City, Calif.) according to manufacturer's instructions. cDNA was amplified using Taqman Universal Master Mix and Taqman Gene Expression Assays which were pre-loaded onto custom Taqman Arrays (Applied Biosystems). Data were analyzed using Sequence Detection Software (Applied Biosystems) and normalized to undifferentiated human embryonic stem (hES) cells using the ΔΔCt method. All primers were purchased from Applied Biosystems.

TABLE I

List of factors tested at S5 of Example 1

| Protein | Concentration | R & D Systems Catalogue Number |
|---|---|---|
| Epigen | 20 ng/ml | 6629-EP-025 |
| Semaphorin 3a | 50 ng/ml | 1250-S3-025 |
| Netrin 4 | 100 ng/ml | 1254-N4-025 |
| Galectin-8 | 100 ng/ml | 1305-GA-050 |
| Tryptase-Y-1 | 20 ng/ml | 1667-SE-010 |
| BetaCellulin | 20 ng/ml | 261-CE-010 |
| Lumican | 100 ng/ml | 2846-LU-050 |
| Epimorphin | 50 ng/ml | 2936-EP-025 |
| Mesothelin | 50 ng/ml | 3265-MS-050 |
| Matrilin-4 | 100 ng/ml | 3380-MN-050 |
| Meteorin | 50 ng/ml | 3475-MN-025 |
| Ephrin-A4 | 100 ng/ml | 369-EA |
| IBSP | 100 ng/ml | 4014-SP-050 |
| EFG-L6 | 50 ng/ml | 4329-EG-025 |
| R-Spondin-1 | 100 ng/ml | 4645-RS-025 |
| Ephrin-B1 | 100 ng/ml | 473-EB-200 |
| Hepsin | 50 ng/ml | 4776-SE-010 |
| Activin A | 20 ng/ml | 338-AC-010 |
| EphA4 | 50 ng/ml | 6827-A4-050 |
| Neurocan | 100 ng/ml | 6508-NC-050 |
| DKK1 | 100 ng/ml | 5439-DK-010 |
| Kallikrein-4 | 50 ng/ml | 1719-SE-010 |
| EGF | 20 ng/ml | 236-EG-200 |
| BDNF | 20 ng/ml | 248-BD-005 |
| Spinesin | 50 ng/ml | 2495-SE-010 |
| HGF | 20 ng/ml | 294-HG-005 |
| EphB4 | 50 ng/ml | 3038-B4-100 |
| Relaxin1 | 50 ng/ml | 3257-RN-025 |
| Activin C | 20 ng/ml | 4879-AC-010 |
| BMP5 | 20 ng/ml | 615-BMC-020 |
| IGF-1 | 20 ng/ml | 291-G1-200 |

Figure 1G:
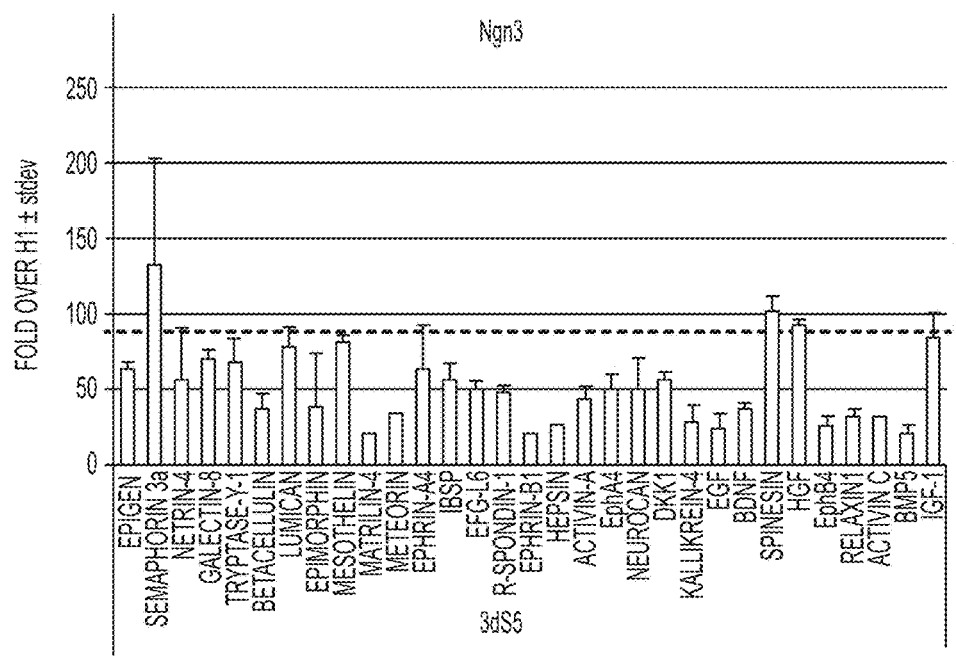

FIG. 1A to FIG. 1G depict data from real-time PCR analyses of the expression of the following genes in cells of the human embryonic stem cell line H1 differentiated to stage 5 as outlined in Example 1 and in the presence of factors listed in Table I: Insulin (FIG. 1A), somatostatin (FIG. 1B), ghrelin (FIG. 1C), glucagon (FIG. 1D), PDX1 (FIG. 1E), NKX6.1 (FIG. 1F), and NGN3 (FIG. 1G).

As shown in FIG. 1, Ephrin-A4 enhanced mRNA expression of NKX6.1 and insulin as compared to control cultures (FIG. 1F) while showing minimal impact on PDX1 (FIG. 1E) and NGN3 expression (FIG. 1G). Factors such as Activin-A and Activin-C significantly enhanced expression of somatostatin (FIG. 1B) while suppressing the expression of insulin (FIG. 1A), glucagon (FIG. 1D), and ghrelin (FIG. 1C). Moreover, factors such as semaphorin 3a and Epigen enhanced NKX6.1 expression while not affecting expression of hormones as compared to untreated cultures. In FIG. 1A to FIG. 1G, the average level of expression of the different markers in control cultures are shown by a dotted line on the graphs.

Example 2

Verification of the Effect of Ephrins on Insulin Expression at S5

This example describes the validation of hits identified in Example 1. In particular, the effect of addition of Ephrin-A3 or Ephrin-A4 at S5 in the protocol listed below.

Cells of the human embryonic stem cell line H1 (hESC H1, passage 40) were seeded as single cells at $1 \times 10^5$ cells/cm$^2$ on MATRIGEL™ (1:30 dilution; BD Biosciences, NJ)-coated dishes in mTeSR®1 media supplemented with 10 µM of Y27632. Forty-eight hours post seeding, cultures were washed in incomplete PBS (phosphate buffered saline without Mg or Ca). Cultures were differentiated into pancreatic endoderm/endocrine lineages as follows:

a) Stage 1 (Definitive Endoderm (DE)—3 days): Cells were cultured for one day in stage 1 media (see Example 1, above). Cells were then cultured for an additional day in MCDB-131 medium supplemented with 0.1% fatty acid-free BSA, 0.0012 g/ml sodium bicarbonate, 1x GlutaMax™, 4.5 mM D-Glucose, 100 ng/ml GDF8, and 0.1 µM MCX compound. Cells were then cultured for an additional day in MCDB-131 medium supplemented with 0.1% fatty acid-free BSA, 0.0012 g/ml sodium bicarbonate, 1x GlutaMax™, 4.5 mM D-Glucose, and 100 ng/ml GDF8, then b) Stage 2 (Primitive gut tube—2 days): Cells were treated for two days with MCDB-131 medium supplemented with 0.1% fatty acid-free BSA; 0.0012 g/ml sodium bicarbonate; 1x GlutaMax™; 4.5 mM D-Glucose; 0.25 mM ascorbic acid (Sigma, Mo.) and 25 ng/ml FGF7 (R & D Systems, MN), then c) Stage 3 (Foregut—2 days): Cells were treated with MCDB-131 medium supplemented with a 1:200 dilution of ITS-X (Invitrogen, Ca); 4.5 mM Glucose; 1x GlutaMax™; 0.0017 g/ml sodium bicarbonate; 2% fatty acid-free BSA; 0.25 µM SANT-1 (Sigma, Mo.); 10 ng/ml of Activin-A (R& D Systems, MN); 1 µM RA (Sigma, Mo.); 25 ng/ml FGF7; 0.25 mM ascorbic acid; 200 nM TPB (PKC activator; Catalog No. 565740; EMD Chemicals, Gibstown, N.J.); 10 µM forskolin and 100 nM LDN (BMP receptor inhibitor; Catalog No. 04-0019; Stemgent) for day 1. On day 2, cells were treated with MCDB-131 medium supplemented with a 1:200 dilution of ITS-X; 4.5 mM Glucose; 1x GlutaMax™; 0.0017 g/ml sodium bicarbonate; 2% fatty acid-free BSA; 0.25 µM SANT-1; 10 ng/ml of Activin-A; 1 µM RA; 25 ng/ml FGF7; 0.25 mM ascorbic acid, 200 nM TPB, 10 µM forskolin and 10 nM LDN, then d) Stage 4 (Pancreatic foregut precursor—2 days): Cells were treated with MCDB-131 medium supplemented with a 1:200 dilution of ITS-X; 4.5 mM Glucose; 1x GlutaMax™; 0.0015 g/ml sodium bicarbonate; 2% fatty acid-free BSA; 0.25 µM SANT-1; 50 nM RA; 50 nM LDN-193189; 10 µM forskolin; 0.25 mM ascorbic acid; and 100 nM TPB for two days, then e) Stage 5 (Pancreatic endoderm/endocrine—3 days): Stage 4 cells were treated with MCDB-131 medium supplemented with a 1:200 dilution of ITS-X; 4.5 mM Glucose; 1x GlutaMax™; 0.0015 g/ml sodium bicarbonate; 2% fatty acid-free BSA; 0.25 µM SANT-1; 50 nM RA; 10 µM forskolin; 0.25 mM ascorbic acid; 100 nM ALk5 inhibitor (for days 2-3 only) (SD-208, disclosed in Molecular Pharmacology 2007, 72:152-161) and +/-0-100 ng/ml of Ephrin-A3 or Ephrin-A4 (R & D systems, MN) for three days.

Figure 2A:
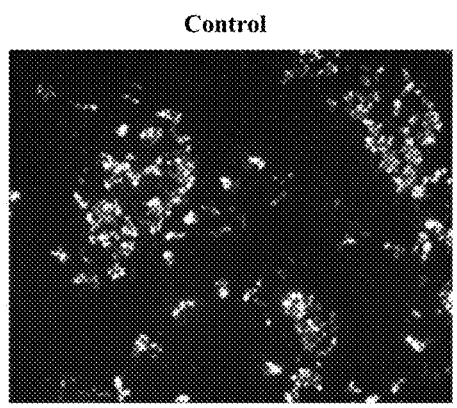
FIG. 2A to FIG. 2C show images of cells immune stained for insulin.
Figure 2B:
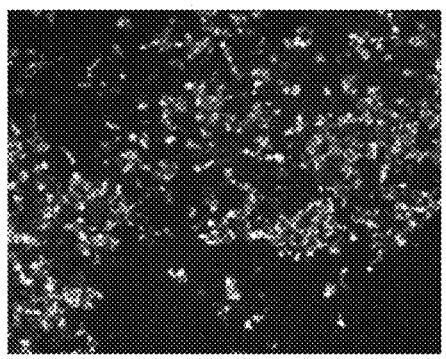
Figure 2C:
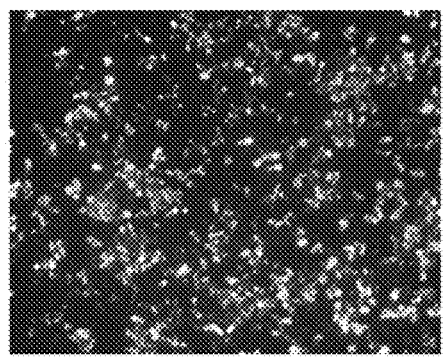
Figure 3A:
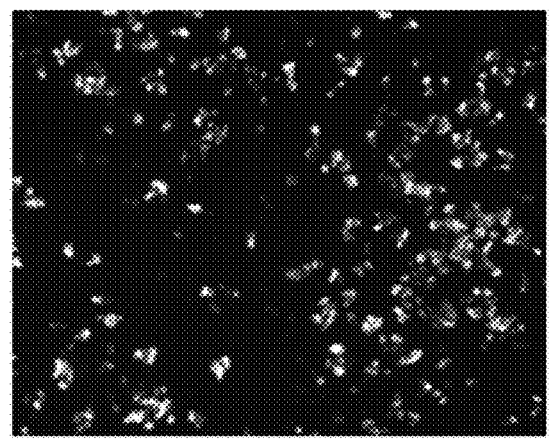
FIG. 3A to FIG. 3C show images of cells immune stained for insulin.
Figure 3B:
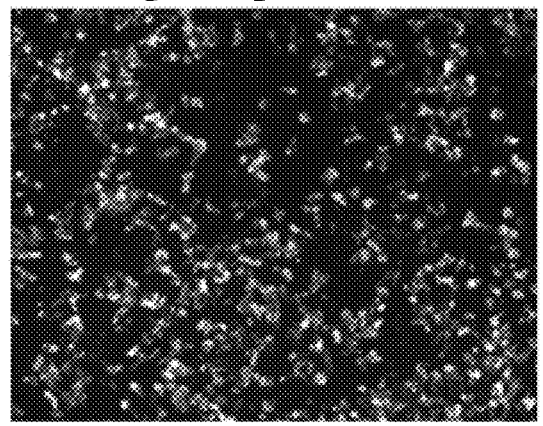
Figure 3C:
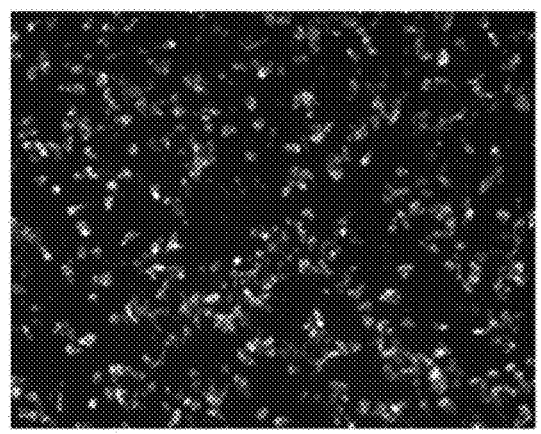

At the end of Stage 5, control and Ephrin-treated cultures were fixed and stained for insulin protein expression (using Guinea Pig anti-insulin antibody from Millipore; Cambridge, Mass.). FIG. 2A to FIG. 2C depict images of cells immunostained for insulin. FIG. 2A, control cells; FIG. 2B, cells treated with 50 ng/ml Ephrin A3; FIG. 2C cells treated with 100 ng/ml Ephrin A3. FIG. 3A to FIG. 3C depicts images of cells immunostained for insulin. FIG. 3A control cells; FIG. 3B, cells treated with 50 ng/ml Ephrin A4; FIG. 3C cells treated with 100 ng/ml Ephrin A4. These data show that, consistent with data from Example 1, addition of both Ephrin-A3 and EphrinA4 at stage 5 significantly enhanced protein expression of insulin.

Example 3

Addition of Sphingosine-1-Phosphate at S6 Significantly Accelerates Formation of Cell Clusters Containing Endocrine Hormones This example describes the progression of endocrine cluster formation at stage 6 and the effect of sphingosine-1-phosphate in accelerating the formation of the endocrine rich clusters.

Cells of the human embryonic stem cell line H1 (hESC H1, passage 40) were seeded as single cells at $1 \times 10^5$ cells/cm$^2$ on MATRIGEL™ (1:30 dilution; BD Biosciences, NJ) coated dishes in mTeSR®1 media (StemCell Technologies, Vancouver, Canada) supplemented with 10 µM of Y27632. Forty-eight hours post seeding, cultures were washed in incomplete PBS (phosphate buffered saline without Mg or Ca). Cultures were differentiated into pancreatic endoderm/endocrine lineages as follows:

a) Stage 1 (Definitive Endoderm (DE)—3 days): Cells were cultured for one day in stage 1 media (see Example 1, above). Cells were then cultured for an additional day in MCDB-131 medium supplemented with 0.1% fatty acid-free BSA, 0.0012 g/ml sodium bicarbonate, 1x GlutaMax™, 4.5 mM D-Glucose, 100 ng/ml GDF8, and 0.1 µM MCX compound. Cells were then cultured for an additional day in MCDB-131 medium supplemented with 0.1% fatty acid-free BSA, 0.0012 g/ml sodium bicarbonate, 1x GlutaMax™, 4.5 mM D-Glucose, and 100 ng/ml GDF8, then b) Stage 2 (Primitive gut tube—2 days): Cells were treated for two days with MCDB-131 medium supplemented with 0.1% fatty acid-free BSA; 0.0012 g/ml sodium bicarbonate; 1x GlutaMax™; 4.5 mM D-Glucose; 0.25 mM ascorbic acid (Sigma, Mo.) and 25 ng/ml FGF7 (R & D Systems, MN), then c) Stage 3 (Foregut—2 days): Cells were treated with MCDB-131 medium supplemented with a 1:200 dilution of ITS-X (Invitrogen, Ca); 4.5 mM Glucose; 1x GlutaMax™; 0.0017 g/ml sodium bicarbonate; 2% fatty acid-free BSA; 0.25 µM SANT-1 (Sigma, Mo.); 10 ng/ml of Activin-A (R& D Systems, MN); 1 µM RA (Sigma, Mo.); 25 ng/ml FGF7; 0.25 mM ascorbic acid; 200 nM TPB (PKC activator; Catalog No. 565740; EMD Chemicals, Gibstown, N.J.); 10 µM forskolin (FSK, Sigma, Mo.), and 100 nM LDN (BMP receptor inhibitor; Catalog No. 04-0019; Stemgent, Calif.) for day 1. On day 2, cells were treated with MCDB-131 medium supplemented with a 1:200 dilution of ITS-X;

4.5 mM Glucose; 1× GlutaMax™; 0.0017 g/ml sodium bicarbonate; 2% fatty acid-free BSA; 0.25 µM SANT-1; 10 ng/ml of Activin-A; 1 µM RA; 25 ng/ml FGF7; 0.25 mM ascorbic acid, 200 nM TPB, and 10 nM LDN, then d) Stage 4 (Pancreatic foregut precursor—2 days); Cells were treated with MCDB-131 medium supplemented with a 1:200 dilution of ITS-X; 4.5 mM Glucose; 1× GlutaMax™; 0.0015 g/ml sodium bicarbonate; 2% fatty acid-free BSA; 0.25 µM SANT-1; 50 nM RA; 50 nM LDN-193189; 10 µM forskolin; 0.25 mM ascorbic acid; 2 ng/ml FGF7; 1 ng/ml AA; and 100 nM TPB for two days, then e) Stage 5 (Pancreatic endoderm/endocrine—3 days): Stage 4 cells were treated with MCDB-131 medium supplemented with a 1:200 dilution of ITS-X; 15 mM Glucose; 1× GlutaMax™; 0.0015 g/ml sodium bicarbonate; 2% fatty acid-free BSA; 0.25 µM SANT-1; 50 nM RA; 10 µM forskolin; 0.25 mM ascorbic acid; and 1 ng/ml FGF7 for three days; with the addition of 100 nM ALK5 inhibitor SD-208 at days 2-3 only, then f) Stage 6 (Pancreatic endocrine—3-10 days): Stage 5 cells were treated with MCDB-131 medium supplemented with a 1:200 dilution of ITS-X; 15 mM Glucose; 1× GlutaMax™; 0.0015 g/ml sodium bicarbonate; 2% fatty acid-free BSA; 0.25 µM SANT-1; 50 nM RA; 0.25 mM ascorbic acid; for 3-10 days. In some cultures 10 µM of Sphingosine-1-phosphate (Sigma, Mo.) was added for three days.

Figure 4A:
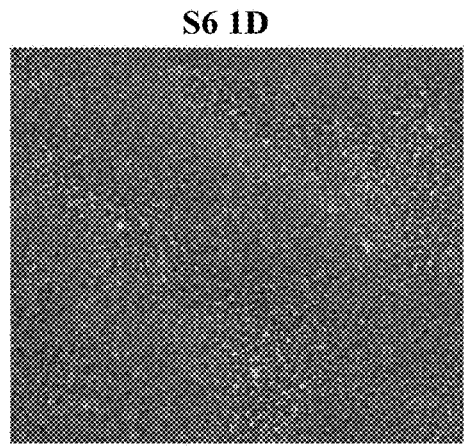
FIG. 4A to FIG. 4D depict phase contrast images of S6 cultures of cells treated with sphingosine-1-phosphate (S1P) and imaged on day 1 (FIG. 4A), day 7 (FIG. 4B), and two different magnifications at day 10 (FIG. 4C and FIG. 4D). The images show that on day 7, there was clear evidence of clustering of endocrine cells and on day 10 the clusters were separated from each other by a thin layer of pancreatic endoderm epithelium.
Figure 4B:
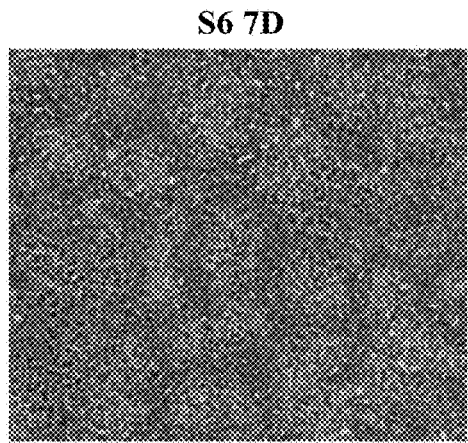
Figure 4C:
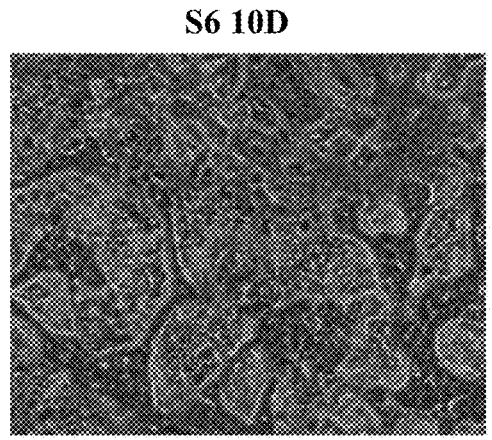
Figure 4D:
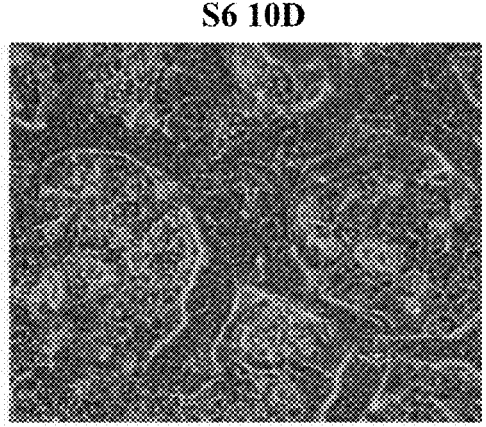

FIG. 4A to FIG. 4D depict phase contrast images of S6 cultures of cells treated with sphingosine-1-phosphate (S1P) and imaged on day 1 (FIG. 4A), day 7 (FIG. 4B), and at two different magnifications at day 10 (FIG. 4C and FIG. 4D). The images show that on day 7, there was clear evidence of clustering of endocrine cells and on day 10 the clusters were separated from each other by a thin layer of pancreatic endoderm epithelium.

Figure 5A:
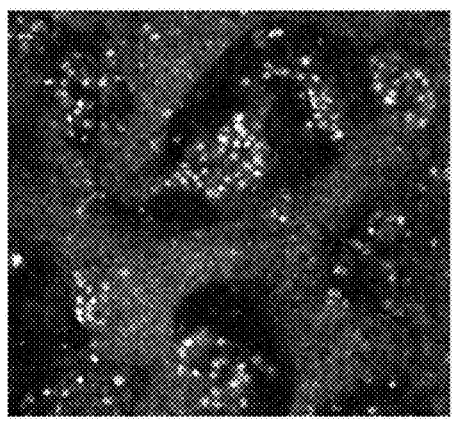
FIG. 5A to FIG. 5D depict images of cells treated with S1P and immunostained for Hb9 (FIG. 5A) and NKX6.1 (FIG. 5B), or immunostained for insulin (FIG. 5C) and Hb9 (FIG. 5D).
Figure 5B:
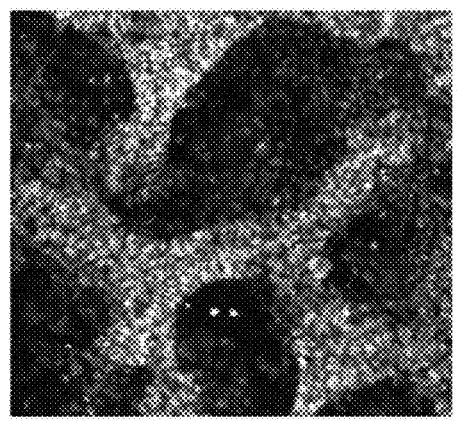
Figure 5C:
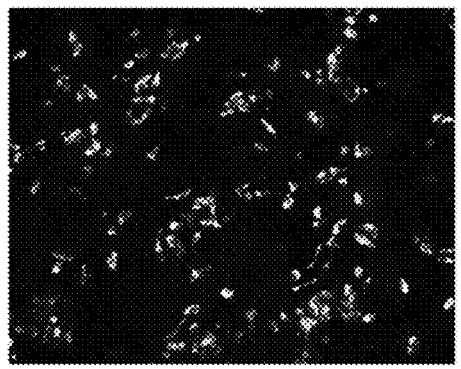
Figure 5D:
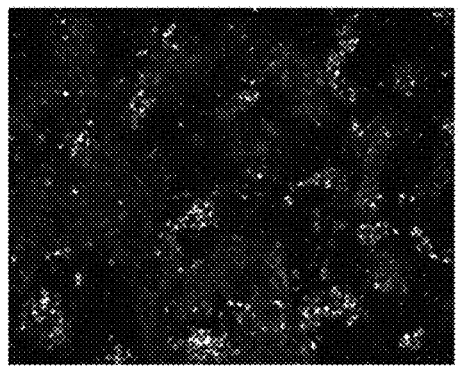

FIG. 5A to FIG. 5D depict images of cells immunostained for Hb9 (FIG. 5A) and NKX6.1 (FIG. 5B), or immunostained for insulin (FIG. 5C) and Hb9 (FIG. 5D). FIG. 5A and FIG. 5B show that the endocrine clusters were enriched for Hb9 while the pancreatic epithelium surrounding the clusters were enriched for NKX6.1. Some of the cells in the Hb9-enriched clusters were also positive for NKX6.1. The clusters were enriched for insulin and Hb9 as shown in FIG. 5C and FIG. 5D. This morphological change closely resembles pancreatic development where NKX6.1+PDX1+ rich epithelium gives rise to endocrine clusters. In each instance, the pair of images was obtained using different filters from the same field of cells.

Figure 6A:
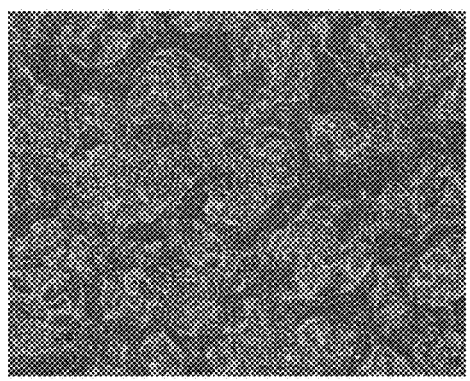
FIG. 6A and FIG. 6B depict phase contrast images, at different magnifications, of cells treated with 10 µM S1P and harvested three days after start of stage 6.
Figure 6B:
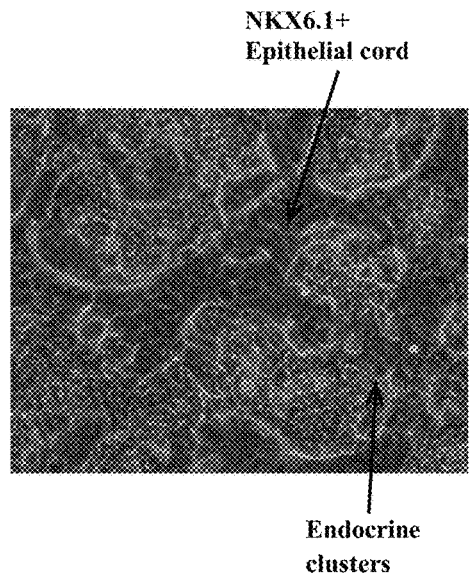

FIG. 6A and FIG. 6B depict phase contrast images, at different magnifications, of cells treated with 10 µM sphingosine-1-phosphate (S1P) and harvested three days after start of stage 6. These images show that endocrine clusters emerged only 3 days after start of stage 6. This is about 7 days earlier than formation of the clusters in control cultures.

Figure 6C:
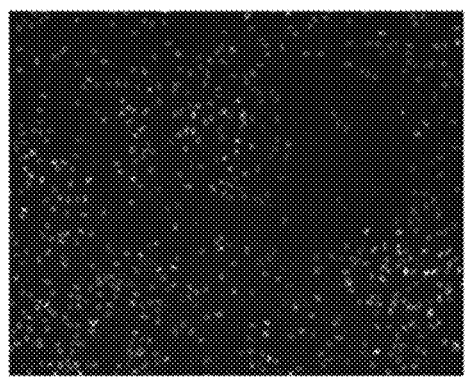
FIG. 6C and FIG. 6D depict images of cells immunostained for NKX2.2.
Figure 6D:
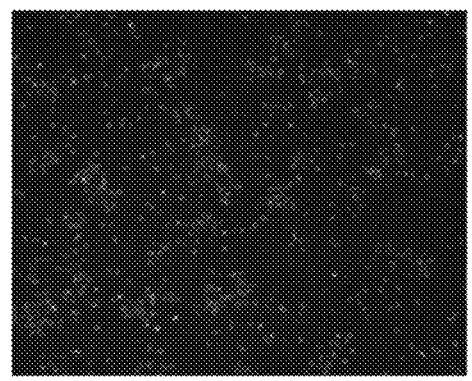

FIG. 6C and FIG. 6D depict images of control cells (FIG. 6C) and cells treated with S1P (FIG. 6D) immunostained for NKX2.2. In S1P-treated cultures, the endocrine clusters were also enriched for NKX2.2+ cells (FIG. 6C), as compared to control cultures where NKX2.2+ cells were distributed uniformly across the culture (FIG. 6D).

What is claimed is:

1. A method of differentiating pancreatic endoderm cells into pancreatic hormone-expressing cells comprising culturing the pancreatic endoderm cells with an Ephrin ligand, wherein the method induces insulin expression.

2. The method of claim 1, wherein culturing the pancreatic endoderm cells with the Ephrin ligand also enhances expression of NKX6.1.

3. The method of claim 2, wherein culturing the pancreatic endoderm cells with an Ephrin ligand enhances expression of insulin and NKX6.1 in the pancreatic endoderm cells when compared with the expression of insulin and NKX6.1 in non-treated pancreatic endoderm cells.

4. The method of claim 3, wherein the pancreatic endoderm cells do not substantially express CDX2 or SOX2.

5. The method of claim 4, wherein the pancreatic endoderm cells express approximately about less than 10% CDX2 or SOX2.

6. The method of any one of claims 1 to 5, wherein the Ephrin ligand is Ephrin A3 or Ephrin A4.

7. The method of claim 6, wherein the pancreatic endoderm cells are obtained by a stepwise differentiation of pluripotent stem cells.

8. The method of claim 7, wherein the pluripotent stem cells are human embryonic pluripotent stem cells.

9. The method of claim 7, wherein the stepwise differentiation comprises differentiating pluripotent stem cells in definitive endoderm cells.

10. The method of claim 7, wherein the stepwise differentiation comprises:
   differentiating pluripotent stem cells into definitive endoderm cells;
   differentiating the definitive endoderm cells into primitive gut tube cells;
   differentiating the primitive gut tube cells into foregut cells;
   differentiating the foregut cells into pancreatic precursor cells; and
   differentiating the pancreatic precursor cells into pancreatic endoderm cells.

11. The method of claim 1, wherein the pancreatic endoderm cells are human pancreatic endoderm cells.

12. A method of differentiating pancreatic endoderm cells into pancreatic endocrine cells comprising treating the pancreatic endoderm cells with an Ephrin ligand.

13. The method of claim 12, wherein the Ephrin ligand is Ephrin A3.

14. The method of claim 12, wherein the Ephrin ligand is Ephrin A4.

* * * * *